(12) United States Patent
Unalmis

(10) Patent No.: US 11,905,825 B2
(45) Date of Patent: Feb. 20, 2024

(54) DOWNHOLE 3-PHASE FLOW MEASUREMENT USING SPEED OF SOUND ABOVE AND BELOW THE BUBBLE-POINT PRESSURE

(71) Applicant: Weatherford Technology Holdings, LLC, Houston, TX (US)

(72) Inventor: Omer Haldun Unalmis, Kingwood, TX (US)

(73) Assignee: WEATHERFORD TECHNOLOGY HOLDINGS, LLC, Houston, TX (US)

( * ) Notice: Subject to any disclaimer, the term of this patent is extended or adjusted under 35 U.S.C. 154(b) by 25 days.

(21) Appl. No.: 17/660,753

(22) Filed: Apr. 26, 2022

(65) Prior Publication Data
US 2023/0340870 A1 Oct. 26, 2023

(51) Int. Cl.
*E21B 47/107* (2012.01)
*G01F 1/66* (2022.01)
*G01F 1/74* (2006.01)
*G01N 33/28* (2006.01)

(52) U.S. Cl.
CPC ............ *E21B 47/107* (2020.05); *G01F 1/666* (2013.01); *G01F 1/74* (2013.01); *G01N 33/2823* (2013.01)

(58) Field of Classification Search
CPC .......... E21B 47/107; G01F 1/666; G01F 1/74; G01N 33/2823
See application file for complete search history.

(56) References Cited

U.S. PATENT DOCUMENTS

| | | |
|---|---|---|
| 6,601,458 B1 | 8/2003 | Gysling et al. |
| 6,945,095 B2 | 9/2005 | Johansen |
| 7,059,172 B2 | 6/2006 | Gysling |
| 7,526,966 B2 | 5/2009 | Gysling et al. |
| 7,607,361 B2 | 10/2009 | Unalmis et al. |
| 7,654,155 B2 | 2/2010 | Johansen et al. |
| 9,347,310 B2 | 5/2016 | Unalmis et al. |

(Continued)

OTHER PUBLICATIONS

Unalmis, O. H., "Flow Measurement Optimization Using Surface Measurements and Downhole Sound Speed Measurements from Local or Distributed Acoustic Sensors," SPE Prod & Oper 36 (02), May 12, 2021, pp. 437-450.

(Continued)

*Primary Examiner* — Kristina M Deherrera
*Assistant Examiner* — Jean F Morello
(74) *Attorney, Agent, or Firm* — Cabello Hall Zinda, PLLC

(57) ABSTRACT

Methods and apparatus for hydrocarbon monitoring are provided. An example method (e.g., performed by a monitoring system) includes receiving one or more first downhole measurements including a first speed of sound (SoS) measurement of a flowing fluid at a first location, wherein a pressure of the flowing fluid at the first location is greater than a bubble-point pressure of the flowing fluid; receiving one or more second downhole measurements including a second SoS measurement of the flowing fluid at a second location, wherein a pressure of the flowing fluid at the second location is less than the bubble-point pressure of the flowing fluid and wherein the flowing fluid is a 3-phase fluid mixture at the second location; and calculating one or more phase flow rates of the 3-phase fluid mixture, based on the first SoS measurement, the second SoS measurement, and a measurement of a bulk velocity of the flowing fluid.

22 Claims, 8 Drawing Sheets

(56) References Cited

U.S. PATENT DOCUMENTS

| | | |
|---|---|---|
| 9,383,476 B2 | 7/2016 | Trehan et al. |
| 2003/0136186 A1 | 7/2003 | Gysling |
| 2014/0076547 A1* | 3/2014 | Unalmis ............... E21B 47/113 |
| | | 166/250.01 |
| 2018/0231498 A1 | 8/2018 | Amir et al. |
| 2021/0381867 A1 | 12/2021 | Unalmis |

OTHER PUBLICATIONS

Haldun, U. O, "Downhole Three-Phase Flow Measurement Using Sound Speed Measured by Local or Distributed Acoustic Sensing", Society of Petroleum Engineers, SPE-210072-MS, Sep. 26, 2022, XP093064165, 20-pgs.

Int'l Search Report and Written Opinion in counterpart PCT Appl. PCT/US2023/014661, dated Jul. 27, 2023, 13-pgs.

* cited by examiner

DOWNHOLE 3-PHASE FLOW
MEASUREMENT USING SPEED OF SOUND
ABOVE AND BELOW THE BUBBLE-POINT
PRESSURE

FIELD OF THE DISCLOSURE

Aspects of the present disclosure generally relate to hydrocarbon production and, more particularly, to deriving phase component fractions and determining phase flow rates for a 3-phase fluid mixture flowing in a conduit.

DESCRIPTION OF THE RELATED ART

In the petroleum industry, as in many other industries, ability to monitor flow of fluids in process pipes in real-time offers considerable value. Oil and gas operators measure individual oil, water, and/or gas flow rates within an overall production flow stream containing a mixture of these three phase components. This information may be used to improve and optimize well production, allocate royalties, prevent corrosion based on the amount of water, and/or determine the well performance.

Determining the phase flow rates in a 3-phase flow may involve several measurements, including measuring speed of sound (SoS). Distributed acoustic sensing (DAS) is one technology that may be used in measuring flow in wells. A DAS system is usually capable of measuring SoS, and depending on its installation, configuration, and the type of application, a DAS system may also be capable of measuring flow velocity.

While an in-well optical flowmeter (OFM) may be used to accurately measure 1- and 2-phase flows by measuring flow velocity and speed of sound (SoS), such an OFM is typically unable to accurately measure 3-phase flows without the use of secondary pressure and temperature sensors. The secondary pressure and temperature sensors may be vertically separated from the OFM and are used to predict the density of the fluid mixture. The measurements of flow velocity, SoS, and mixture density are sufficient for solving 3-phase flows. However, the 3-phase solution from such a system has been found to be inaccurate when the gas volume fraction (GVF) of the flow is greater than 30%.

It is therefore desirable to develop techniques for measuring 3-phase flows in wells having a GVF greater than 30%.

SUMMARY

Certain aspects of the present disclosure provide a method for hydrocarbon monitoring. The method generally includes receiving one or more first downhole measurements including a first speed of sound (SoS) measurement of a flowing fluid at a first location, wherein a pressure of the flowing fluid at the first location is greater than a bubble-point pressure of the flowing fluid; receiving one or more second downhole measurements including a second SoS measurement of the flowing fluid at a second location, wherein a pressure of the flowing fluid at the second location is less than the bubble-point pressure of the flowing fluid and wherein the flowing fluid is a 3-phase fluid mixture at the second location; and calculating one or more phase flow rates of the 3-phase fluid mixture, based on the first SoS measurement, the second SoS measurement, and a measurement of a bulk velocity of the flowing fluid.

According to certain aspects, the method further includes determining a first inline phase fraction of the flowing fluid at the first location based on the first downhole measurements. For some aspects, the first inline phase fraction is a water-in-liquid ratio (WLR). For other aspects, the first downhole measurements further comprise a temperature of the flowing fluid at the first location and a pressure of the flowing fluid at the first location; and determining the first inline phase fraction of the flowing fluid at the first location is based on the first speed of sound (SoS) measurement, the temperature of the flowing fluid at the first location, the pressure of the flowing fluid at the first location, and single-phase properties of components of the flowing fluid. For still other aspects, determining the first inline phase fraction comprises: calculating a SoS in an infinite medium based on the Wood and Korteweg-Lamb equations and the first downhole measurements; and determining the first inline phase fraction based on the SoS in the infinite medium, the first downhole measurements, and single-phase properties of components of the flowing fluid.

According to certain aspects, the second downhole measurements further comprise a temperature of the flowing fluid at the second location, a pressure of the flowing fluid at the second location, and the measurement of the bulk velocity of the flowing fluid at the second location. For some aspects, the method further includes determining a first inline phase fraction of the flowing fluid at the first location based on the first downhole measurements; and determining an inline liquid volume fraction (LVF) of the flowing fluid, based on the first inline phase fraction or a second inline phase fraction, the second downhole measurements, and single-phase properties of components of the flowing fluid. For some aspects, determining the LVF of the flowing fluid is based on the first inline phase fraction. For other aspects, the method further includes determining the second inline phase fraction based on the first inline phase fraction, the temperatures of the flowing fluid at the first and second locations, and the pressures of the flowing fluid at the first and second locations, wherein determining the LVF of the flowing fluid is based on the second inline phase fraction. For still other aspects, determining the inline LVF comprises: calculating a speed of sound (SoS) in an infinite medium based on the Wood and Korteweg-Lamb equations and the second downhole measurements; and determining the inline LVF based on the SoS in the infinite medium, the second downhole measurements, and the single-phase properties of components of the flowing fluid. For yet other aspects, the method further includes determining the single-phase properties of components of the flowing fluid based on an analysis of a bottom hole fluid sample.

According to certain aspects, the first location and the second location are a same location; receiving the first downhole measurements comprises receiving the first downhole measurements at a first time when the pressure is greater than the bubble-point pressure; and receiving the second downhole measurements comprises receiving the second downhole measurements at a second time when the pressure is less than the bubble-point pressure, the second time being different from the first time.

According to certain aspects, at least one of the first downhole measurements or the second downhole measurements is received from an optical flowmeter.

According to certain aspects, at least one of the first downhole measurements or the second downhole measurements is received from a distributed acoustic sensing (DAS) coil.

Certain aspects of the present disclosure provide a processing system for hydrocarbon monitoring. The processing system is configured to receive one or more first downhole measurements including a first speed of sound (SoS) measurement of a flowing fluid at a first location, wherein a pressure of the flowing fluid at the first location is greater than a bubble-point pressure of the flowing fluid; receive one or more second downhole measurements including a second SoS measurement of the flowing fluid at a second location, wherein a pressure of the flowing fluid at the second location is less than the bubble-point pressure of the flowing fluid and wherein the flowing fluid is a 3-phase fluid mixture at the second location; and calculate one or more phase flow rates of the 3-phase fluid mixture, based on the first SoS measurement, the second SoS measurement, and a measurement of a bulk velocity of the flowing fluid.

Certain aspects of the present disclosure provide a non-transitory computer-readable medium (e.g., a computer-readable storage device). The computer-readable medium generally includes instructions which, when executed by a processing system, cause the processing system to perform operations for hydrocarbon monitoring. The operations generally include receiving one or more first downhole measurements including a first speed of sound (SoS) measurement of a flowing fluid at a first location, wherein a pressure of the flowing fluid at the first location is greater than a bubble-point pressure of the flowing fluid; receiving one or more second downhole measurements including a second SoS measurement of the flowing fluid at a second location, wherein a pressure of the flowing fluid at the second location is less than the bubble-point pressure of the flowing fluid and wherein the flowing fluid is a 3-phase fluid mixture at the second location; and calculating one or more phase flow rates of the 3-phase fluid mixture, based on the first SoS measurement, the second SoS measurement, and a measurement of a bulk velocity of the flowing fluid.

Certain aspects of the present disclosure provide a method for modifying a hydrocarbon monitoring system comprising an optical flowmeter disposed at a first location in a well and a processing system, wherein a pressure of a flowing fluid at the first location is less than a bubble-point pressure of the flowing fluid and wherein the flowing fluid is a 3-phase fluid mixture at the first location. The method generally includes: introducing a sensor into the well such that the sensor is disposed at a second location in the well, wherein a pressure of the flowing fluid at the second location is greater than the bubble-point pressure of the flowing fluid; and configuring the processing system to calculate one or more phase flow rates of the 3-phase fluid mixture, based on a first speed of sound (SoS) measurement of the flowing fluid at the first location received from the optical flowmeter, a second SoS measurement of the flowing fluid at the second location received from the sensor, and a measurement of a bulk velocity of the flowing fluid.

According to certain aspects, the sensor comprises an optical waveguide of a distributed acoustic sensing (DAS) system. For some aspects, introducing the sensor comprises introducing the optical waveguide of the DAS system on a same optical waveguide communicatively coupled to the optical flowmeter. For some aspects, the optical waveguide comprises a DAS coil or DAS line and wherein introducing the sensor comprises disposing the DAS coil or DAS line at the second location.

According to certain aspects, introducing the sensor comprises introducing a distributed acoustic sensing (DAS) waveguide into the well, separate from a waveguide communicatively coupled to the optical flowmeter.

According to certain aspects, configuring the processing system further comprises configuring the processing system to calculate the one or more phase flow rates based on measurements of pressure and temperature of the flowing fluid at the second location.

BRIEF DESCRIPTION OF THE DRAWINGS

So that the manner in which the above-recited features of the present disclosure can be understood in detail, a more particular description of the disclosure, briefly summarized above, may be had by reference to aspects, some of which are illustrated in the appended drawings. It is to be noted, however, that the appended drawings illustrate only typical aspects of this disclosure and are therefore not to be considered limiting of its scope, for the disclosure may admit to other equally effective aspects.

Identical reference numerals have been used, where possible, to designate identical elements that are common to the figures.

DETAILED DESCRIPTION

Figure 1:
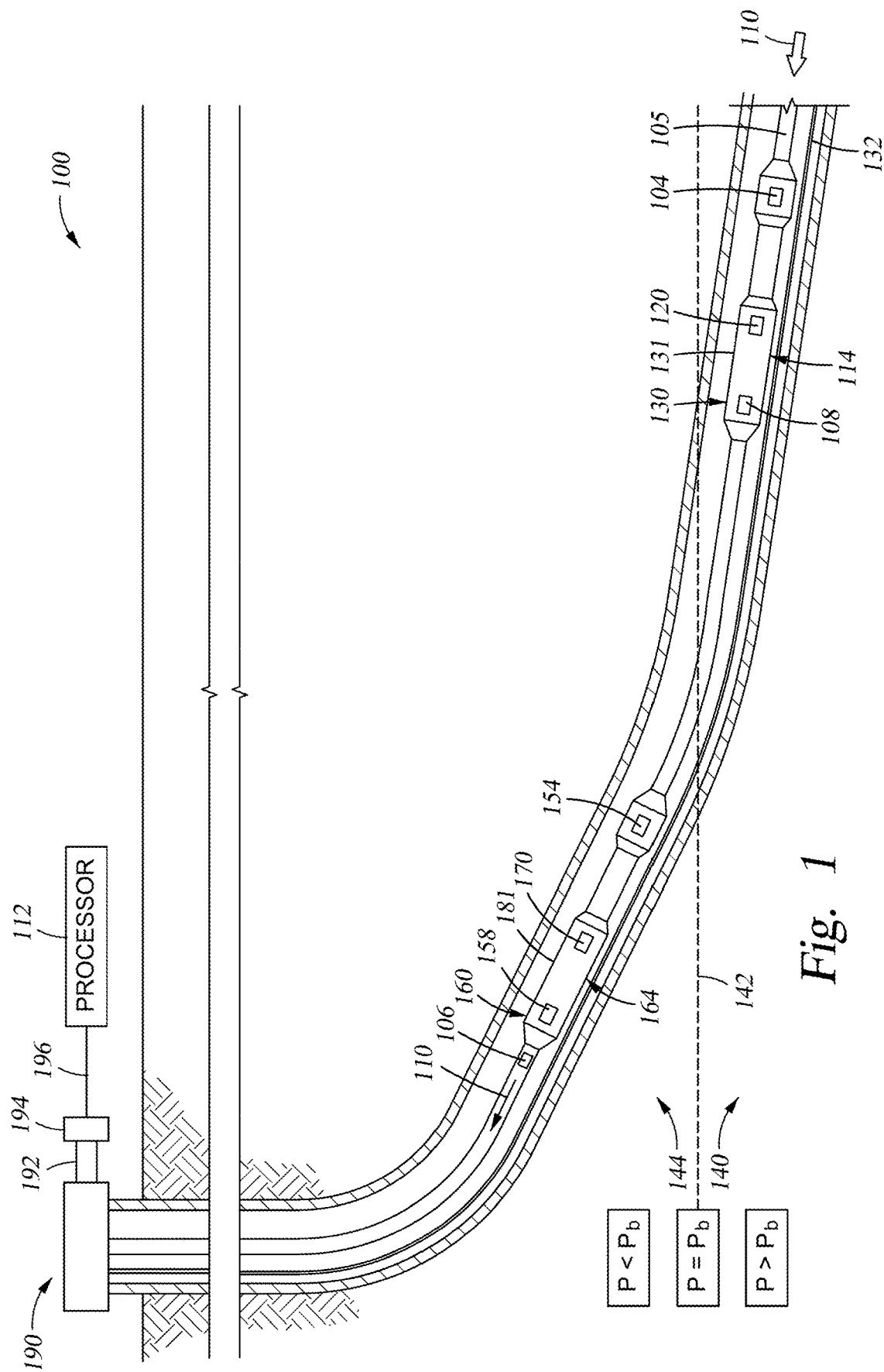
FIG. 1 illustrates an example system that may be utilized to perform multiphase flow rate measurements, according to aspects of the present disclosure.

Certain aspects of the present disclosure provide techniques and apparatus for monitoring hydrocarbons by deriving downhole phase fractions and determining downhole flow rates for individual phases of a 3-phase flow. The techniques and apparatus derive downhole phase fractions and flow rates based on several parameters at two locations: a first location where the pressure in the fluid is greater than the bubble-point pressure ($P_b$) of the fluid and a second location where the pressure in the fluid is less than $P_b$. At the first location, a first downhole pressure ($P_1$), a first downhole temperature ($T_1$), and a first speed of sound ($SoS_1$) of the mixture are measured, and at the second location, a second downhole pressure ($P_2$), a second downhole temperature ($T_2$), a second speed of sound ($SoS_2$) of the mixture, and a downhole flow velocity of the mixture are measured. The described parameters may be directly measured and used to derive downhole phase fractions and flow rates of each phase of a 3-phase flow.

The techniques and apparatus for deriving downhole phase fractions and determining downhole phase flow rates may be based on measuring or receiving one or more first downhole measurements including a first speed of sound (SoS) measurement of a flowing fluid at a first location, wherein a pressure of the flowing fluid at the first location is greater than a bubble-point pressure of the flowing fluid; receiving one or more second downhole measurements including a second SoS measurement of the flowing fluid at a second location, wherein a pressure of the flowing fluid at the second location is less than the bubble-point pressure of the flowing fluid and wherein the flowing fluid is a 3-phase fluid mixture at the second location; and calculating one or more phase flow rates of the 3-phase fluid mixture, based on the first SoS measurement, the second SoS measurement, and a measurement of a bulk velocity of the flowing fluid.

Previously known downhole flowmeters typically consist of Venturi-type devices, which are typically suitable for single-phase flows and have limited flow rate ranges due to their low turndown ratios (i.e., ratio of maximum flow rate to minimum flow rate). Because these devices measure single-phase flows, such devices do not provide important measurements, such as a water cut measurement, that typically involve measurements of two-phase flow rates.

Some technologies involving distributed acoustic sensing (DAS) may be used for downhole monitoring. A DAS system is typically capable of measuring SoS and, depending on its installation, configuration, and the type of application, a DAS system may also be capable of measuring flow velocity. However, data acquisition in a DAS system for the complete length of fiber usually leads to extremely large amounts of data, and thus, a selective process and reduction of data are desirable. In the current state of DAS technology, the data is usually post-processed and not reported in real-time.

As used herein, in a 3-phase fluid mixture, both "oil phase" and "oil" refer to non-water-soluble hydrocarbons in the 3-phase fluid mixture. Also as used herein, in a 3-phase fluid mixture, both "water phase" and "water" refer to a mixture of water and water-soluble materials in the 3-phase fluid mixture. Finally, as used herein, in a 3-phase fluid mixture, both "gas phase" and "gas" refer to a mixture of gaseous materials that have come out of solution from the water phase and/or the oil phase and formed bubbles.

FIG. 1 illustrates an example system 100 that may be utilized to perform multiphase flow rate measurements of a fluid mixture flow 110 (i.e., a fluid flow) in a conduit 105 in accordance with aspects of the present disclosure. For example, the conduit 105 may be production tubing disposed in a wellbore. A line 142 indicates a depth at which pressure (P) of the fluid mixture in the conduit 105 is equal to a bubble-point pressure ($P_b$) of the fluid mixture. When the fluid mixture is exposed to the bubble-point pressure or a lower pressure, the fluid mixture effervesces as gas(es) dissolved within the fluid mixture escape from solution. Pressure of the fluid mixture in the conduit 105 is expected to be greater than $P_b$ in a region 140 that is generally deeper than the line 142. Pressure of the fluid mixture in the conduit 105 is expected to be less than $P_b$ in a region 144 that is generally shallower than the line 142. Thus, the fluid mixture in the conduit 105 may be expected to effervesce as the fluid mixture moves from the region 140 into the region 144.

As illustrated, the example system 100 includes, at a first location 114, a first flowmeter 130 that includes at least one first pressure sensor 108 (e.g., a static pressure sensor) and at least one first temperature sensor 120 in one section 131 for measuring pressure at the first location 114 ($P_1$) and temperature of the fluid mixture at the first location 114 ($T_1$). The pressure sensor may be any suitable type of sensor that measures pressure directly, such as a diaphragm configured to flex and apply a force to an optical waveguide (e.g., an optical fiber) within the flowmeter 130. The at least one temperature sensor 120 may measure the mixture temperature at or near the same point (e.g., location 114) at which pressure is sensed by the pressure sensor 108.

The first location 114 is selected to be within region 140, such that pressure of the fluid mixture within the conduit 105 is greater than the bubble-point pressure ($P_b$) for the fluid mixture. Thus, the fluid mixture flowing at the first location 114 is a 2-phase mixture, as the fluid mixture will not effervesce due to the pressure in the fluid mixture being greater than $P_b$. The first flowmeter 130 also includes a first SoS meter 104 that allows measurement of SoS of the fluid mixture in the conduit at the first location 114 ($SoS_1$). Pressure, temperature, and SoS measurements taken from the sensors may be used to calculate a water-in-liquid ratio (WLR) of the fluid mixture, as described herein. The WLR of the fluid mixture may then be used in calculating flow rates for the 3-phase fluid mixture, as explained in more detail below.

The flowmeter 130 may be an optical flowmeter (OFM) or an electrical flowmeter. While illustrated with a flowmeter 130, the example system 100 is not so limited, and may include a sound measurement system (electronic or optical) for determining a fluid flow rate, such as a distributed acoustic sensing (DAS) system, which may include an optical waveguide 132.

The example system 100 includes, at a second location 164, a second flowmeter 160 that includes at least one second pressure sensor 158 (e.g., a static pressure sensor) and at least one second temperature sensor 170 in one section 181 for measuring pressure of the fluid at the second location 164 ($P_2$) and temperature of the fluid mixture at the second location 164 ($T_2$). The at least one second temperature sensor 170 may measure the mixture temperature at or near the same point (e.g., second location 164) at which pressure is sensed by the second pressure sensor 158. The second pressure sensor 158 may or may not be identical to the first pressure sensor 108. Similarly, the second temperature sensor 170 may or may not be identical to the first temperature sensor 120.

The second location 164 is selected to be within region 144, such that pressure of the fluid mixture within the conduit 105 is less than the bubble-point pressure ($P_b$) for the fluid mixture. Thus, the fluid mixture flowing at the second location 164 is a 3-phase mixture, as the fluid mixture effervesces due to the pressure in the fluid mixture being less than $P_b$. The second flowmeter 160 also includes a second SoS meter 154 that allows measurement of SoS of the fluid mixture in the conduit at the second location 164 ($SoS_2$).

The system 100 also includes a fluid bulk velocity sensor 106 that measures the bulk velocity of the flowing fluid mixture. The bulk velocity of the flowing fluid mixture may be used in calculating flow rates for the 3-phase flow. In some cases, one or more of the first SoS meter 104, the second SoS meter 154, and the bulk velocity sensor 106 may include a pressure sensor array. For some aspects, the bulk velocity sensor 106 may be located at the second location 164 and may be part of the second flowmeter 160, as illustrated in FIG. 1. For other aspects, a bulk velocity sensor may additionally or alternatively be located at the first location 114 and may be separate from or part of the flowmeter 130.

An example of the first SoS meter 104 or the second SoS meter 154 may include two or more sensing elements that form an array. Spacing between the sensing elements may enable sensing acoustic signals traveling at the SoS through the fluid flow 110 within the conduit 105 (referred to as "acoustic sensing") and can also enable sensing short duration local pressure variations traveling with the fluid flow (referred to as "flow velocity sensing"). The acoustic signals and/or the local pressure variations commonly originate from naturally occurring phenomena. For some aspects, the sensor elements may be formed with optical fiber in the flowmeter 130 within the conduit 105. Other pressure-measuring devices, such as piezoelectric- or polyvinylidene fluoride (PVDF)-based detectors, may also be used.

The system 100 may include an analyzer 194 to determine single-phase properties of components of fluid from the well. For example, the analyzer 194 may determine density and SoS, at various temperatures and pressures, for single-phase gas components of the fluid from the well. In another example, the analyzer 194 may determine density and SoS, at various temperatures and pressures, for single-phase oil components of the fluid from the well. For some aspects, the analyzer 194 may be part of the processor 112. For other aspects, the system 100 may not include an analyzer.

The system 100 may also include one or more sensors (e.g., pressure and/or temperature sensors) at a wellhead 190 or separator 192 of the well.

A processor 112 may receive signals conveying measurements from the flowmeters 130 and 160, sensors at the wellhead 190 or separator 192, and/or the analyzer 194 via one or more cables 196 or wirelessly. The cables 196 may, for example, include optical waveguides and/or electric wires. The processor 112 may obtain single-phase properties of components of fluid from the well directly from the analyzer 194 or from a database of the single-phase properties of components of fluid from the well. The database may be populated with the single-phase properties of components of fluid from the well based on analysis performed by the analyzer 194.

Example Techniques for Deriving Downhole
3-Phase Component Fractions and Determining
Downhole 3-Phase Flow Rates Aspects of the present disclosure use measurements of speed of sound (SoS) of a fluid at a first location, where pressure of the fluid is above the bubble-point pressure ($P_1 > P_b$) of the fluid, and a second location, where pressure of the fluid is below the bubble-point pressure ($P_2 < P_b$), combined with pressure and temperature measurements to calculate phase flow rates of a 3-phase flow. The calculation process uses the SoS, pressure, and temperature measurements at the first location to derive a downhole phase fraction. The downhole phase fraction is used with the SoS, pressure, and temperature measurements at the second location, and a measurement of bulk velocity of the fluid to calculate the phase flow rates in the 3-phase flow.

While examples of the techniques described herein feature optical flowmeters, the present disclosure is not limited to using optical flowmeters. Measurements from sensors using various technologies may be used in calculating phase flow rates in a 3-phase flow. For example, measurements from optical flowmeters, distributed acoustic sensing (DAS) systems, distributed temperature sensing (DTS) systems, distributed pressure sensing (DPS) systems, Venturi flowmeters, differential pressure (DP) gauges, pressure gauges, and temperature gauges may be used in the techniques described herein. Table 1, below, lists various types of sensor technologies that may be used in resolving 3-phase flow rates, as well as their measurement capabilities.

TABLE 1

Downhole Sensors and Measurements

Figure 2:
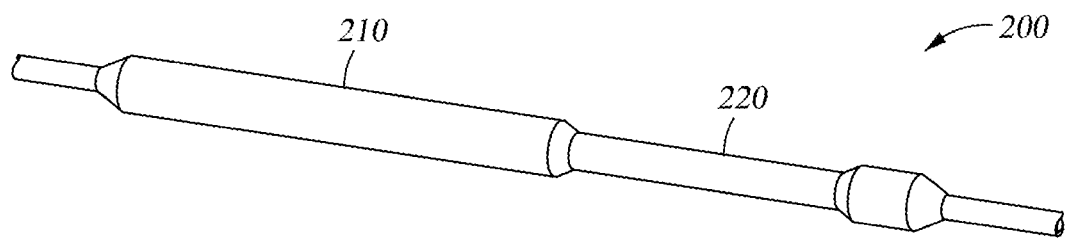
FIG. 2 illustrates an example optical flowmeter, for use with aspects of the present disclosure.
Figure 3:
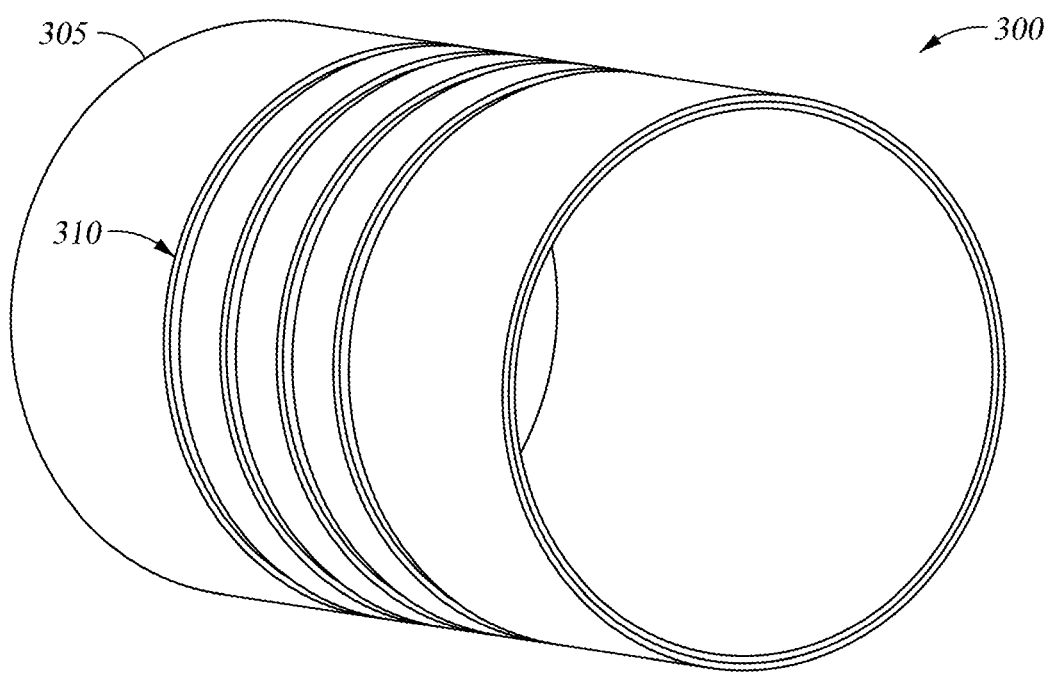
FIG. 3 illustrates an example distributed acoustic sensing (DAS) sensor in a coiled or helical configuration, for use with aspects of the present disclosure.
Figure 4:
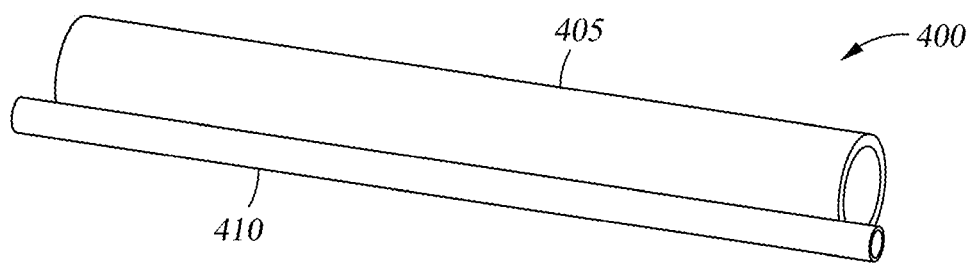
FIG. 4 illustrates an example DAS sensor in a linear configuration, for use with aspects of the present disclosure.
Figure 5:
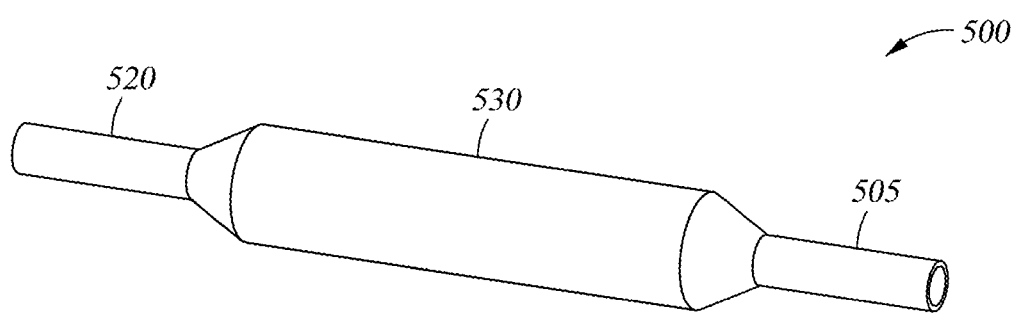
FIG. 5 illustrates an example Venturi flowmeter, for use with aspects of the present disclosure.
Figure 6:
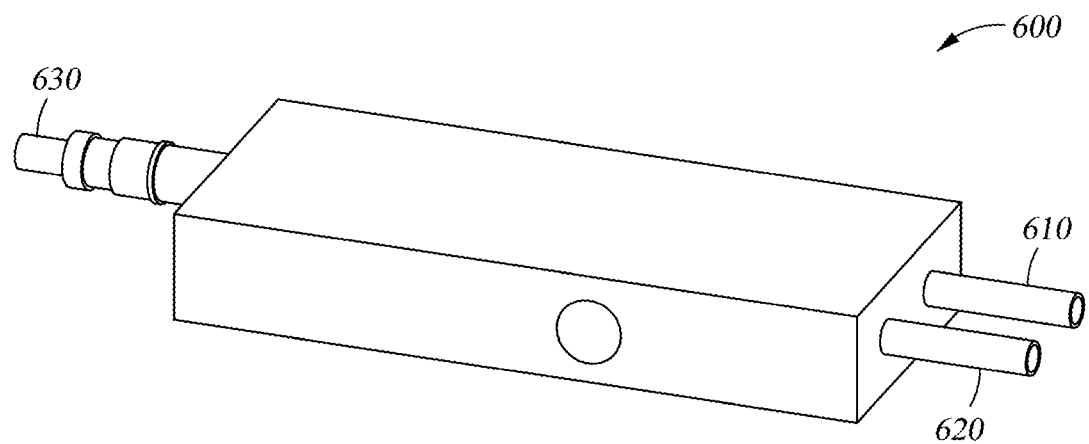
FIG. 6 illustrates an example delta pressure (DP) gauge, for use with aspects of the present disclosure.

| Sensors | Measurements |
| --- | --- |
| Optical flowmeter (OFM) with integrated P/T gauge, as shown in FIG. 2 | SoS, Velocity, P, T |
| Distributed acoustic sensing system, coil or helical configuration ($DAS_{coil}$), as shown in FIG. 3 | SoS, Velocity |
| Distributed acoustic sensing system, linear configuration ($DAS_{line}$), as shown in FIG. 4 | SoS |
| Distributed temperature sensing system (DTS) | T |
| Distributed pressure sensing system (DPS) | P |
| Venturi flowmeter, as shown in FIG. 5 | $\Delta P = P_1 - P_2$ |
| DP gauge, as shown in FIG. 6 | $\Delta P = P_1 - P_2$ |
| Pressure gauge | P |
| Temperature gauge | T |

FIG. 2 illustrates an example optical flowmeter 200, for use with aspects of the present disclosure. The optical flowmeter 200 includes a first section 210 that includes pressure and temperature sensors and a second section 220 that includes sensors for measuring the velocity of the flow and SoS in the fluid. The optical flowmeter 200 may measure SoS in the fluid in the conduit, bulk fluid velocity, pressure of the fluid, and temperature of the fluid.

FIG. 3 illustrates an example distributed acoustic sensing (DAS) sensor 300 in a coiled or helical configuration, for use with aspects of the present disclosure. The DAS sensor 300 includes an optical waveguide 310 in a coiled or helical configuration around a conduit 305 conveying the fluid being sensed. The DAS sensor 300 may measure SoS in the fluid in the conduit 305 and bulk fluid velocity of the fluid. The conduit 305 may be an example of the conduit 105 shown in FIG. 1.

FIG. 4 illustrates an example DAS sensor 400 in a linear configuration, for use with aspects of the present disclosure. The example DAS sensor 400 includes an optical waveguide 410 in a linear configuration paralleling and contacting a conduit 405 conveying the fluid being sensed. The example DAS sensor 400 may measure SoS in the fluid in the conduit 405. In some cases, the optical waveguide includes a protective coating, such that the actual optical-wave-carrying medium (e.g., an optical fiber) is acoustically coupled to, but indirectly contacts the conduit 405. The conduit 405 may be an example of the conduit 105 shown in FIG. 1. While the example DAS sensor 400 includes an optical waveguide 410 contacting the outside of a conduit 405 conveying the fluid being sensed, the present disclosure is not so limited. Aspects of the present disclosure may be practiced with a DAS sensor that includes an optical waveguide disposed within a conduit and directly contacts the fluid being sensed. In some cases, the optical waveguide includes a protective coating, such that the actual optical-wave-carrying medium is acoustically coupled to, but indirectly contacts, the fluid being sensed within the conduit.

FIG. 5 illustrates an example Venturi flowmeter 500, for use with aspects of the present disclosure. The Venturi flowmeter 500 is typically installed in-line with a conduit 505 conveying the fluid being sensed. The Venturi flowmeter 500 may measure a differential pressure between a first location 520 and a second location 530 that have two different cross-sectional areas. The conduit 505 may be an example of the conduit 105 shown in FIG. 1.

FIG. 6 illustrates an example differential pressure (DP) gauge 600, for use with aspects of the present disclosure. The DP gauge 600 may be installed in connection with a conduit (e.g., conduit 105, shown in FIG. 1) conveying the fluid being sensed. The DP gauge 600 may obtain, via a first input 610, an indication of pressure at a first location. The first input 610 may, for example, be a tube connecting to the first location such that the DP gauge 600 is in fluid communication with the first location. The DP gauge 600 may also obtain, via a second input 620, an indication of pressure at a second location. The second input 620 may, for example, be another tube connecting to the second location such that the DP gauge 600 is in fluid communication with the second location. The DP gauge 600 may measure a differential pressure between the first location and the second location. The DP gauge 600 may report the differential pressure via an output 630. The DP gauge 600 may report the differential pressure optically (e.g., via a fiber-optic cable) or electronically (e.g., via a wire).

According to aspects of the present disclosure, various sensor configurations may be used for 3-phase flow measurement. 3-phase flow measurement may be accomplished based on a first SoS measurement ($SoS_1$) at a first station where pressure ($P_1$) of the fluid is greater than the fluid's bubble-point pressure ($P_b$), a second SoS measurement ($SoS_2$) at a second station where pressure ($P_2$) of the fluid is less than the fluids bubble-point pressure ($P_b$), a first measurement of pressure ($P_1$) of the fluid at the first station, a second measurement of pressure ($P_2$) of the fluid at the second station, a first measurement of temperature ($T_1$) of the fluid at the first station, a second measurement of temperature ($T_2$) of the fluid at the second station, and a measurement of the bulk velocity (e.g., the bulk velocity $V_2$ of the fluid at the second station). Table 2, below, shows some example sensor configurations that may be used for 3-phase flow measurement.

TABLE 2

Example Sensor Configurations for 3-Phase Flow Measurement

| Config-uration | Station 1 sensor(s) | Station 2 sensor(s) | Measurements |
|---|---|---|---|
| 1 | $DAS_{line}$, P gauge, and T gauge | $DAS_{coil}$, P gauge, and T gauge | $SoS_1$, $SoS_2$, $V_2$, $P_1$, $P_2$, $T_1$, and $T_2$ |
| 2 | $DAS_{line}$, DTS, and DPS | $DAS_{coil}$, DTS, and DPS | $SoS_1$, $SoS_2$, $V_2$, $P_1$, $P_2$, $T_1$, and $T_2$ |
| 3 | $DAS_{line}$, P gauge, and T gauge | OFM | $SoS_1$, $SoS_2$, $V_2$, $P_1$, $P_2$, $T_1$, and $T_2$ |
| 4 | $DAS_{line}$, P gauge, and T gauge | $DAS_{line}$, P gauge, T gauge, and Venturi | $SoS_1$, $SoS_2$, $V_2$, $P_1$, $P_2$, $T_1$, and $T_2$ |
| 5 | $DAS_{line}$, P gauge, and T gauge | $DAS_{line}$, P gauge, T gauge, and DP gauge | $SoS_1$, $SoS_2$, $V_2$, $P_1$, $P_2$, $T_1$, and $T_2$ |
| 6 | OFM | OFM | $SoS_1$, $SoS_2$, $V_1$, $V_2$, $P_1$, $P_2$, $T_1$, and $T_2$ |

With reference to Table 2, above, the described configurations and extensions of those configurations are described as follows. Configuration 1 is an all-DAS solution at both stations. The $DAS_{coil}$ configuration may be utilized for velocity measurements. Because one velocity is sufficient for the described calculations of 3-phase flow rates, the DAS configuration at the first station may be a $DAS_{line}$ (i.e., a $DAS_{line}$ may be used at Station 1, as the 3-phase flow rates may be calculated without a measurement of $V_1$). While a DAS system may measure SoS and velocities, P and T may be measured by any suitable type of pressure gauge and temperature gauge. In one configuration, a single optical fiber may be sufficient for a DAS system that has pressure and temperature sensors at both stations.

Configuration 2 is an all-distributed-sensing solution using a $DAS_{line}$ and a $DAS_{coil}$ for SoS and velocity measurements, a DTS for temperature measurements at both locations, and a DPS for pressure measurements at both locations.

Configuration 3 is a solution which combines the power of OFM and DAS technologies. The solution may be implemented with a single optical fiber implemented as a combination $DAS_{line}$ system, pressure sensor, and temperature sensor at the first station that measures $SoS_1$, $P_1$, and $T_1$. The OFM may measure $SoS_2$, $P_2$, $T_2$, and $V_2$ at the second station.

Configuration 4 uses a $DAS_{line}$, pressure sensors, and temperature sensors at both stations, while $V_2$ at the second station is measured by a single-phase Venturi flowmeter.

Configuration 5 uses a $DAS_{line}$ and P/T sensors at both stations while $V_2$ at the second station is measured by a DP sensor that measures $\Delta P$ between two different cross-sectional areas at the second station. A DP sensor may use a single $\Delta P$ sensor that senses a difference in pressure between two locations or may use two separate pressure sensors and report a difference between the measured pressures. The two different cross-sectional areas could, for example, refer to an upstream (i.e., inlet) location and a downstream (i.e., outlet) location of an inflow control valve (ICV) element, such that the cross-sectional area at the upstream location could be the cross-sectional area of the conduit (e.g., conduit 105, shown in FIG. 1), and the cross-sectional area at the downstream location could be the cross-sectional area of one of the smaller openings of the ICV.

Configuration 6 is an all-OFM solution, using an OFM at each station. At each station, SoS, V, P, and T may be measured. In such a case, when the OFMs are installed in a multi-zone well, the phase flow rates produced by the lower zone may be obtained by blocking the upper zone production. That is, such a system may determine phase flow rates of a lower zone in a multi-zone well when the upper zone is blocked from producing.

Figure 7:
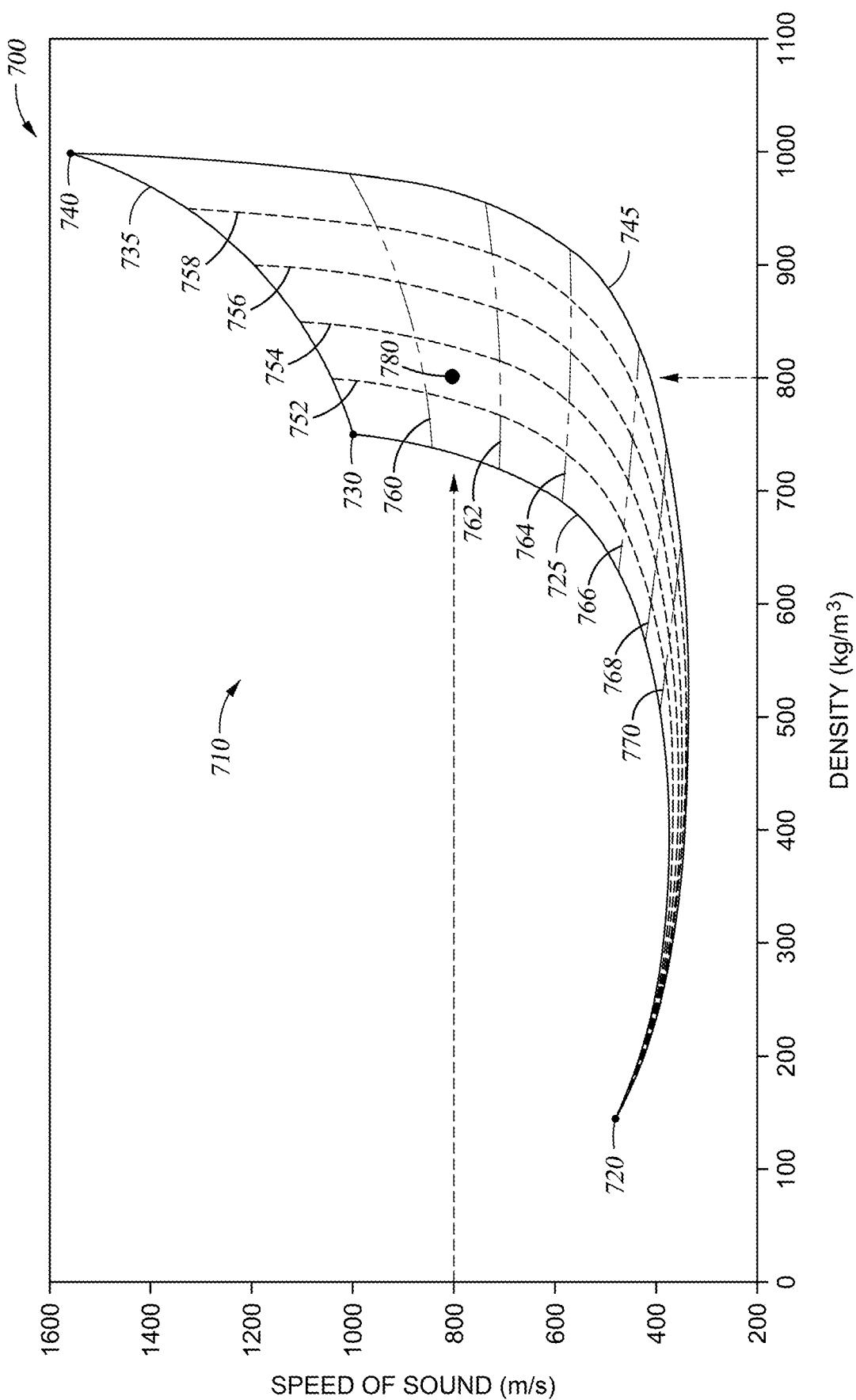
FIG. 7 illustrates a graph of an example solution envelope in the density and speed of sound domain for a 3-phase flow, in accordance with aspects of the present disclosure.

FIG. 7 illustrates a graph 700 of an example solution envelope 710 in the density and speed of sound (SoS) domain for a 3-phase flow, in accordance with aspects of the present disclosure. The solution envelope 710 may be determined from an analysis of fluid from a well, e.g., an analysis performed by analyzer 194 of fluid from a wellbore at which the system 100, shown in FIG. 1, is implemented. The graph 700 includes a first point 720 that is located at the density and SoS of a single-phase flow of the gases present in the 3-phase flow. That is, if a flow of only the gases present in the 3-phase flow was separated from the 3-phase flow and was at the same pressure and temperature as the 3-phase flow, that (gas-phase only) flow would have the density and SoS shown at the first point 720. The graph 700 also includes a second point 730 that is located at the density and SoS of a single-phase flow of the oil present in the 3-phase flow. That is, if a flow of only the oil present in the 3-phase flow was separated from the 3-phase flow and was at the same pressure and temperature as the 3-phase flow, that (oil-phase only) flow would have the density and SoS shown at the second point 730. The graph 700 also includes a third point 740 that is located at the density and SoS of a single-phase flow of the water present in the 3-phase flow. Similar to the first point 720 and the second point 730, if a flow of only the water present in the 3-phase flow was separated from the 3-phase flow and was at the same pressure and temperature as the 3-phase flow, that (water-phase only) flow would have the density and SoS shown at the third point 740. The density and SoS values of points 720, 730, and 740 may be obtained from tabulated values determined from a sample fluid analysis performed by analyzer 194.

The solution envelope 710 is bound by three 2-phase curves 725, 735, and 745. Curve 725 represents the SoS and density of 2-phase mixtures of gas and oil having various proportions of gas and oil. The curve 725 approaches point 720 as the proportions of a 2-phase mixture of gas and oil approach limits of 100% gas and 0% oil, while the curve 725 approaches point 730 as proportions of a 2-phase mixture of gas and oil approach limits of 0% gas and 100% oil.

Curve 735 represents the SoS and density of 2-phase mixtures of oil and water having various proportions of oil and water. The curve 735 approaches point 730 as proportions of a 2-phase mixture of oil and water approach limits of 100% oil and 0% water, while the curve 735 approaches point 740 as proportions of a 2-phase mixture of oil and water approach limits of 0% oil and 100% water.

Curve 745 represents the SoS and density of 2-phase mixtures of water and gas having various proportions of water and gas. The curve 745 approaches point 740 as proportions of a 2-phase mixture of water and gas approach limits of 100% water and 0% gas, while the curve 745 approaches point 720 as proportions of a 2-phase mixture of water and gas approach limits of 0% water and 100% gas.

The curves 725, 735, and 745 that bound the solution envelope 710 can be obtained by calculating the mixture density based on volumetric phase fractions using Equation (1) and calculating SoS for the mixture using the Wood equation, Equation (2):

$$\rho_m = (1-\phi)\rho_1 + \phi\rho_2 \tag{1}$$

$$SoS_m = \left\{[(1-\phi)\rho_1 + \phi\rho_2]\left[\frac{1-\phi}{\rho_1 a_1^2} + \frac{\phi}{\rho_2 a_2^2}\right]\right\}^{-1/2} \tag{2}$$

where
$\rho_m$: density of mixture
$\rho_1$: density of phase 1 (i.e., gas, oil, or water phase)
$\beta_2$: density of phase 2 (i.e., gas, oil, or water phase)
$SoS_m$: speed of sound of mixture in the infinite medium
$\alpha_1$: SoS of phase 1 in the infinite medium
$\alpha_2$: SoS of phase 2 in the infinite medium
$\phi$: volumetric phase fraction between two phases [0-1]

By systematically varying the volumetric phase fraction $\phi$ from 0 to 1 with a reasonable resolution, ($\mu_m$, $SoS_m$) pairs may be calculated. When $\phi=0$ (i.e., 100% phase 1), this corresponds to the pair ($\rho_1$, $\alpha_1$); when $\phi=1$ (i.e., 100% phase 2), this corresponds to the pair ($\rho_2$, $\alpha_2$). Using this process between phases 1 and 2, 2 and 3, and 1 and 3 enables calculating points on the curves 725, 735, and 745 (e.g., boundaries) of the solution envelope 710 shown in FIG. 7. The phases 1, 2, and 3 may be arbitrarily selected to represent oil, water, and gas, respectively. Thus, the pairs ($\rho_0$, $\alpha_0$) (i.e., oil density and SoS), ($\rho_w$, $\alpha_w$) (i.e., water density and SoS), and ($\rho_g$, $\alpha_g$) (i.e., gas density and SoS) represent the 1-phase oil, 1-phase water, and 1-phase gas conditions, respectively (i.e., the corners at points 730, 740, and 720, respectively, of the 3-phase solution envelope 710).

The graph 700 includes water-in-liquid ratio (WLR) contours 752, 754, 756, and 758 and liquid volume fraction (LVF) contours 760, 762, 764, 766, 768, and 770. The WLR contours 752, 754, 756, and 758 intersect the curve 735 of the oil and water 2-phase solution, whereas the LVF contours 760, 762, 764, 766, 768, and 770 are approximately parallel to the curve 735 of the 2-phase oil and water solution and intersect the two gas and liquid curves (i.e., the curve 725 of the gas and oil 2-phase solution and the curve 745 of the 2-phase gas and water solution). While the curves 725, 735, and 745 (e.g., boundaries) of the 3-phase solution envelope 710 may be obtained using the 2-phase versions of the density and SoS equations, Equations (1) and (2), the contours of LVF and WLR may be obtained based on calculations using more general versions of Equations (1) and (2) that involve all three phases. Equations (3) and (4) below are the more general versions of Equations (1) and (2) that involve all three phases:

$$\rho_m = (1-WLR)(LVF)\rho_o + (WLR)(LVF)\rho_w + (1-LVF)\rho_g \tag{3}$$

$$SoS_m = \left\{\rho_m\left[\frac{(LVF)(1-WLR)}{\rho_o a_o^2} + \frac{(LVF)(WLR)}{\rho_w a_w^2} + \frac{(1-LVF)}{\rho_g a_g^2}\right]\right\}^{-1/2} \tag{4}$$

Equations (3) and (4) may be derived as follows. The relationship between the volumetric fractions of pure phase components in a multiphase flow mixture (i.e., oil, water, and gas) follows Equation (5):

$$\phi_o + \phi_w + \phi_g = 1 \tag{5}$$

where $\phi$ represents the volumetric fraction and the indices "o, w, g" represent the oil, water, and gas phases, respectively.

The phase fractions, liquid volume fraction (LVF), which represents the total liquid amount in a flowing fluid mixture, and water-in-liquid ratio (WLR), which represents the amount of water in the total liquid flow, may be derived as shown in equations (6) and (7):

$$LVF = \frac{\phi_o + \phi_w}{\phi_o + \phi_w + \phi_g} = \phi_o + \phi_w \tag{6}$$

$$WLR = \frac{\phi_w}{\phi_o + \phi_w} = \frac{\phi_w}{LVF} \tag{7}$$

The volumetric phase fractions $\phi_o$, $\phi_w$, and $\phi_g$ can be written in terms of phase fractions LVF and WLR, as shown in Equations (8), (9), and (10):

$$\phi_o = (1-WLR)(LVF) \tag{8}$$

$$\phi_w = (WLR)(LVF) \tag{9}$$

$$\phi_g = (1-LVF) \tag{10}$$

The mixture density at a meter location downhole is given by Equation (11):

$$\rho_m = \phi_o \rho_o + \phi_w \rho_w + \phi_g \rho_g \tag{11}$$

Substituting Equations (8), (9), and (10) into Equation (11) gives Equation (12), which is the same as Equation (3):

$$\rho_m = (1-WLR)(LVF)\rho_o + (WLR)(LVF)\rho_w + (1-LVF)\rho_g \tag{12}$$

Fluid compressibility is related to density and speed of sound (SoS) per Equation (13):

$$\kappa = \frac{1}{\rho a^2} \tag{13}$$

where:
- κ: compressibility of the fluid;
- ρ: density of the fluid; and
- α: SoS in the infinite fluid medium.

When dealing with multiphase flows, the typical approach is to use a volumetric proportion of each phase to calculate the mixture compressibility. In a 3-phase well-mixed flow of oil/water/gas, the compressibility of the mixture, Km, can be written as Equation (14):

$$\kappa_m = \phi_o \kappa_o + \phi_w \kappa_w + \phi_g \kappa_g \quad (14)$$

where K is the compressibility of a fluid, $\phi$ is a volumetric phase fraction, and the subscripts m, o, w, and g refer to mixture, oil, water, and gas, respectively.

The mixture compressibility can be expressed in terms of volumetric phase fractions, densities, and speed of sound (SoS) of phases by applying Equation (13) to Equation (14), as shown in Equation (15):

$$\frac{1}{\rho_m a_m^2} = \frac{\phi_o}{\rho_o a_o^2} + \frac{\phi_w}{\rho_w a_w^2} + \frac{\phi_g}{\rho_g a_g^2} \quad (15)$$

The SoS values, $\alpha_m$, $\alpha_o$, $\alpha_w$, and $\alpha_g$ in Equation (15) are for the infinite medium of mixture, oil, water, and gas, respectively. Equation (15) is sometimes referred to as the Wood equation. Equation (15) can be rewritten using the phase fractions LVF and WLR from Equations (8), (9), and (10), as shown in Equation (16):

$$\frac{1}{\rho_m a_m^2} = \frac{(LVF)(1-WLR)}{\rho_o a_o^2} + \frac{(LVF)(WLR)}{\rho_w a_w^2} + \frac{(1-LVF)}{\rho_g a_g^2} \quad (16)$$

Since $\alpha_m$ and $SoS_m$ each refer to the speed of sound of the mixture in the infinite medium, i.e., $\alpha_m = SoS_m$, Equation (16) may be rearranged to derive Equation (4).

Referring again to FIG. 7, the LVF contours 760, 762, 764, 766, 768, and 770 and the WLR contours 752, 754, 756, and 758 can now be plotted using Equations (3) and (4) (or Equations (12) and (16)) by keeping one of LVF or WLR at a constant value (i.e., at the "contour" value) between 0 and 1 and varying the other of LVF or WLR, with a reasonable resolution, from 0 to 1. In this manner, pairs of ($\mu_m$, $SoS_m$) values at constant LVF or WLR contour values may be calculated.

Point 780 is an example 3-phase solution point for an example fluid flow (e.g., fluid flow 110, shown in FIG. 1). Point 780 is located in the 3-phase solution envelope 710. The 3-phase point 780 corresponds to a specific pair of (LVF, WLR) values. The 3-phase point 780 also corresponds to a specific pair of ($\mu_m$, $SoS_m$) values. Thus, the 3-phase point 780 is associated with four parameters which are related to each other according to Equations (3) and (4). Knowing (e.g., by measuring) two of the four parameters enables solving the system of Equations (3) and (4) to determine the other two parameters.

Note that $SoS_m$ refers to the mixture SoS in the infinite medium, whereas the SoS measurement is made in the pipe. For a confined area, such as a pipe or conduit, the SoS measured by a flowmeter may be different from the SoS for the infinite medium, since the measured SoS will carry the compliance effects. The relation between the SoS in the infinite medium and the SoS in the pipe is given by the Korteweg-Lamb equation, shown as Equation (17):

$$\frac{1}{\rho_m a_p^2} = \frac{1}{\rho_m a_m^2} + \left(\frac{d}{t}\right)\left(\frac{1-v^2}{E}\right) \quad (17)$$

where:
- $\alpha_p$: speed of sound of mixture in the pipe;
- $\alpha_m$: speed of sound of mixture in the infinite medium;
- d: pipe diameter;
- t: pipe wall thickness;
- E: modulus of elasticity of pipe material; and
- v: Poisson ratio of pipe material (~0.3 for rigid bodies, such as steel).

The Korteweg-Lamb equation (Equation (17)) can be rewritten by incorporating the Wood equation (Equation (4) or Equation (16)), as shown in Equation (18):

$$\frac{1}{\rho_m a_p^2} = \frac{(LVF)(1-WLR)}{\rho_o a_o^2} + \frac{(LVF)(WLR)}{\rho_w a_w^2} + \frac{(1-LVF)}{\rho_g a_g^2} + \left(\frac{d}{t}\right)\left(\frac{1-v^2}{E}\right) \quad (18)$$

where $\rho_m$, $\rho_o$, $\rho_w$, and $\mu_g$ refer to the mixture, oil, water, and gas densities, respectively.

Equations (3) and (4) can be used to calculate $\mu_m$ and $SoS_m$ as a function of LVF, WLR, $\rho_o$, $\rho_w$, $\mu_g$, $\alpha_o$, $\alpha_w$, and $\alpha_g$.

The expression obtained for $\rho_m$ (Equation (3)) is used in Equation (18) along with the SoS measurement in the pipe, $\alpha_p$, resulting in a quadratic equation, Equation (19), which has two unknowns, WLR and LVF:

$$a_p^2\left[\left(\frac{1}{\rho_m a_p^2} - \frac{1}{\rho_o a_o^2}\right)WLR \cdot LVF + \left(\frac{1}{\rho_o a_o^2} - \frac{1}{\rho_g a_g^2}\right)LVF + \frac{1}{\rho_g a_g^2} + \right. \quad (19)$$
$$\left. \left(\frac{d}{t}\right)\left(\frac{1-v^2}{E}\right)\right][(\rho_w - \rho_o)WLR \cdot LVF + (\rho_o - \rho_g)LVF + \rho_g] - 1 = 0$$

All of the individual phase properties ($\rho_i$ and $\alpha_i$ values) in Equation (19) are obtained from tabulated values based on the fluid sample analysis at different pressures and temperatures (e.g., an analysis made by the analyzer 194, shown in FIG. 1).

The solutions of the quadratic equation (Equation (19)) are explained with reference to Equations (20), (21), (22), (23), (24), and (25) below.

A detailed example of application of the disclosed techniques for calculating 3-phase phase fractions and 3-phase flow rates of a flowing fluid is described below with reference to FIG. 8, in accordance with aspects of the present disclosure. Initially, the operator typically obtains a report of a bottom hole fluid sample analysis. The data in the report is provided to a pressure, volume, and temperature (PVT) software package to create an initial properties file, including single-phase properties of components of the flowing fluid, for use in the calculations by a monitoring system.

A first SoS measurement is made at a depth along the well (i.e., at a location referred to as Station 1) where the pressure is greater than the bubble-point pressure, P>$P_b$, with no free gas in the fluid mixture. This is the SoS measurement at $P_1$ and $T_1$ made in the pipe (i.e., $\alpha_p$ in Equations (17), (18), (19), and others described herein) by the sound measurement system and carries the compliance effects of a closed conduit.

According to aspects of the present disclosure, Equation (19) may be used twice, with data from two different locations, to determine the two unknowns, WLR and LVF, for the 3-phase flow. WLR and LVF may then be used with a measurement of bulk velocity of the flowing fluid to determine one or more phase flow rates of the 3-phase flow.

Equation (19) may be used once with first downhole measurements of a 3-phase flow of a fluid at a first location (e.g., location 114, shown in FIG. 1), where $P>P_b$. Because $P>P_b$, the fluid mixture has no free gas. Substituting LVF=1 into Equation (19) results in Equation (20):

$$a_p^2\left[\left(\frac{1}{\rho_w a_w^2} - \frac{1}{\rho_o a_o^2}\right)WLR + \frac{1}{\rho_o a_o^2} + \left(\frac{d}{t}\right)\left(\frac{1-v^2}{E}\right)\right] \quad (20)$$
$$[(\rho_w - \rho_o)WLR + \rho_o] - 1 = 0$$

which may be solved for WLR.

Equation (20) is of the same form as Equation (21):

$$(A \cdot WLR + B) \times (C \cdot WLR + D) - 1 = 0, \text{ where} \quad (21)$$

$$A: a_p^2\left(\frac{1}{\rho_w a_w^2} - \frac{1}{\rho_o a_o^2}\right);$$

$$B: a_p^2\left\{\frac{1}{\rho_o a_o^2} + \left(\frac{d}{t}\right)\left(\frac{1-v^2}{E}\right)\right\};$$

$$C: (\rho_w - \rho_o); \text{ and}$$

$$D: \rho_o.$$

Equation (21) may be rearranged as Equation (22):

$$WLR^2 + \frac{(AD + BC)}{AC} \cdot WLR + \frac{BD - 1}{AC} = 0. \quad (22)$$

Setting $(AD+BC)/AC=\beta$ and $BD-1/AC=\lambda$ and solving Equation (22), using the quadratic formula, for example, results in finding that the two solutions for WLR are:

$$WLR_1 = \frac{-\beta + \sqrt{\beta^2 - 4\lambda}}{2} = \left(-\beta + \sqrt{\delta}\right)/2 \text{ and}$$

$$WLR_2 = \frac{-\beta - \sqrt{\beta^2 - 4\lambda}}{2} = \left(-\beta + \sqrt{\delta}\right)/2, \text{ where}$$

$$\beta: \frac{(AD + BC)}{AC};$$

$$\lambda: \frac{BD - 1}{AC};$$

$$\delta: \beta^2 - 4\lambda;$$

$$A: a_p^2\left(\frac{1}{\rho_w a_w^2} - \frac{1}{\rho_o a_o^2}\right);$$

$$B: a_p^2\left\{\frac{1}{\rho_o a_o^2} + \left(\frac{d}{t}\right)\left(\frac{1-v^2}{E}\right)\right\};$$

$$C: (\rho_w - \rho_o); \text{ and}$$

$$D: \rho_o.$$

In aspects of the present disclosure, the negative solution for WLR, $WLR_2$, is invalid for typical oil and water mixtures. That is, while the negative solution of WLR, $WLR_2$, may solve the described equations, $WLR_2$ is not useful for describing real-world fluid flows.

Figure 8:
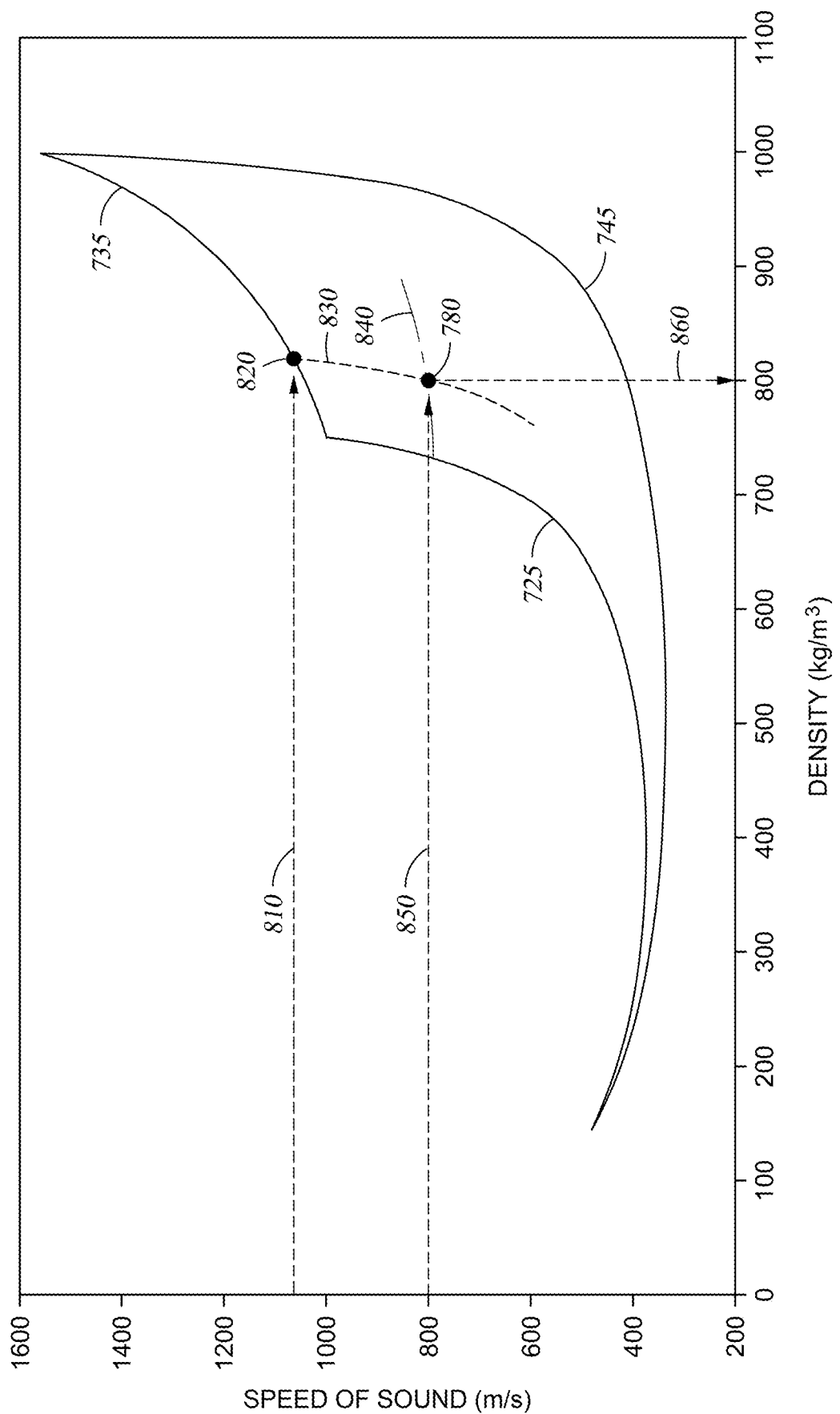
FIG. 8 illustrates a detailed example of calculating 3-phase phase fractions and 3-phase flow rates of a flowing fluid, in accordance with aspects of the present disclosure.

The positive solution for WLR represents the 2-phase point 820 at the intersection of the oil and water 2-phase curve 735 and the WLR contour 830 in FIG. 8. Once WLR is calculated, the corresponding $\rho_m$ is calculated using Equation (3), and the corresponding $SoS_m$ is calculated using Equation (4) or Equation (17). The dashed line at 810 in FIG. 8 represents the $SoS_m$ for the infinite medium at $P_1$ and $T_1$ (i.e., at Station 1).

Once WLR is determined using measurements from the first location, Equation (19) may be used a second time with second downhole measurements of the 3-phase flow of the fluid at a second location where $P<P_b$ (e.g., location 164, shown in FIG. 1) to determine LVF.

Second downhole measurements including a second SoS measurement may be made at a depth (i.e., at a location referred to as Station 2) where the pressure is less than the bubble-point pressure, $P<P_b$, with free gas present in the fluid mixture. This is the SoS measurement at $P_2$ and $T_2$ made in the pipe (i.e., $\alpha_p$ in Equations (17), (18), (19), and others described herein) by the sound measurement system and carries the compliance effects of a closed conduit.

The WLR calculated at Station 1 is used along with the second SoS measurement in the pipe, $\alpha_p$, in Equations (23), (24), and/or (25), described below, to calculate LVF. The LVF contour is represented by contour 840, and the pair of values (LVF, WLR) represents the 3-phase point 780 in FIG. 8. The pair of values (LVF, WLR) may be used to calculate the corresponding $SoS_m$ represented by the dashed line 850, via Equation (4), and the corresponding $\rho_m$ represented by the dashed line 860, via Equation (3). Dashed line 850 represents the $SoS_m$ for the infinite medium at $P_2$ and $T_2$ (i.e., at Station 2).

Equation (19) may be rearranged to solve for LVF, as shown in Equation (23):

$$\left[a_p^2\left\{\left(\frac{1}{\rho_w a_p^2} - \frac{1}{\rho_o a_o^2}\right)WLR + \frac{1}{\rho_o a_o^2} - \frac{1}{\rho_g a_g^2}\right\}LVF + \right. \quad (23)$$
$$\left. a_p^2\left\{\frac{1}{\rho_g a_g^2} + \left(\frac{d}{t}\right)\left(\frac{1-v^2}{E}\right)\right\}\right][\{(\rho_w - \rho_o)WLR + \rho_o - \rho_g\}LVF + \rho_g] - 1 = 0$$

Equation (23) is of the same form as Equation (24):

$$(A' \cdot LVF + B') \times (C' \cdot LVF + D') - 1 = 0, \text{ where} \quad (24)$$

$$A': a_p^2\left\{\left(\frac{1}{\rho_w a_w^2} - \frac{1}{\rho_o a_o^2}\right)WLR + \frac{1}{\rho_o a_o^2} - \frac{1}{\rho_g a_g^2}\right\};$$

$$B': a_p^2\left\{\frac{1}{\rho_w a_w^2} + \left(\frac{d}{t}\right)\left(\frac{1-v^2}{E}\right)\right\};$$

$$C': \{(\rho_w - \rho_o)WLR + \rho_o - \rho_g\}; \text{ and}$$

$$D': \rho_g.$$

Equation (24) may be rearranged as Equation (25):

$$LVF^2 + \frac{(A'D' + B'C')}{A'C'} \cdot LVF + \frac{B'D' - 1}{A'C'} = 0. \quad (25)$$

Setting $$\frac{(A'D' + B'C')}{A'C'} = \beta' \text{ and } \frac{B'D' - 1}{A'C'} = \lambda'$$

and solving Equation (25), using the quadratic formula, for example, results in finding that the two solutions for LVF are:

$$LVF_1 = \frac{-\beta' + \sqrt{\beta'^2 - 4\lambda'}}{2} = (\beta' + \sqrt{\delta'})/2 \text{ and}$$

$$LVF_2 = \frac{-\beta' + \sqrt{\beta'^2 - 4\lambda'}}{2} = (-\beta' - \sqrt{\delta'})/2, \text{ where}$$

$$\beta': \frac{(A'D' + B'C')}{A'C'};$$

$$\lambda': \frac{B'D' - 1}{A'C'};$$

$$\delta': \beta'^2 - 4\lambda';$$

$$A': a_p^2\left\{\left(\frac{1}{\rho_w a_w^2} - \frac{1}{\rho_o a_o^2}\right)WLR + \frac{1}{\rho_o a_o^2} - \frac{1}{\rho_g a_g^2}\right\};$$

$$B': a_p^2\left\{\frac{1}{\rho_g a_g^2} + \left(\frac{d}{t}\right)\left(\frac{1-v^2}{E}\right)\right\};$$

$$C': \{(\rho_w - \rho_o)WLR + \rho_o - \rho_g\}; \text{ and}$$

$$D': \rho_g.$$

According to aspects of the present disclosure, unlike the solutions for WLR, both solutions of LVF in Equation (25) are valid. The positive solution represents a liquid-rich mixture, whereas the negative solution represents a gas-rich mixture. This is because the curve based on the Wood equation takes a minimum value within the possible LVF range (0 to 1), and thus, for some SoS values, a dual solution corresponding to positive and negative solutions for LVF exists.

In aspects of the present disclosure, calculation of 3-phase flow rates may make use of information provided in a properties file that includes tables of speed of sound and tables of other fluid properties such as density, viscosity, etc. of the individual phases.

According to aspects of the present disclosure, once the inline phase fractions LVF and WLR are determined, the inline phase flow rates can be calculated as follows:

$$Q_{total} = V \cdot \text{Area}$$

$$Q_{oil} = Q_{total} \cdot LVF \cdot (1 - WLR)$$

$$Q_{gas} = Q_{total} \cdot (1 - LVF)$$

$$Q_{water} = Q_{total} \cdot LVF \cdot WLR \quad (26)$$

where Q is the volumetric flow rate, V is a bulk velocity of the fluid, and Area is the cross-sectional area of the pipe where the bulk velocity measurement is made.

The corresponding inline mass flow rates can also be calculated:

$$M_{total} = \rho_m \cdot Q_{total}$$

$$M_{oil} = \rho_o \cdot Q_{oil}$$

$$M_{gas} = \rho_g \cdot Q_{gas}$$

$$M_{water} = \rho_w \cdot Q_{water} \quad (27)$$

where M is the mass flow rate.

In aspects of the present disclosure, the standard phase flow rates can be obtained by using the inline phase flow rates and conversion factors, which may be derived from a pressure, volume, and temperature (PVT) analysis of fluids. The conversion factors may be calculated based on single-phase properties of components of the flowing fluid obtained from analysis of the flowing fluid (e.g., an analysis made by the analyzer 194, shown in FIG. 1). The conversion factors and/or single-phase properties may be stored in a properties file that may be made available to processing systems for hydrocarbon monitoring, as described herein.

The flow rate derivations using Equations (26) and (27) assume well-mixed flows. For gas and liquid flows that are not well mixed, it is also possible to implement various multiphase flow correlations to consider possible slip conditions between the phases. Three example methods include: (1) a homogeneous flow approach in which flow patterns and slippage between the phases are not considered (Equation (26) is based on this approach); (2) an empirical correlation that predicts the liquid holdup and pressure gradient while considering the slippage but not the flow pattern; and (3) another empirical correlation that considers both slippage and flow patterns.

Figure 9:
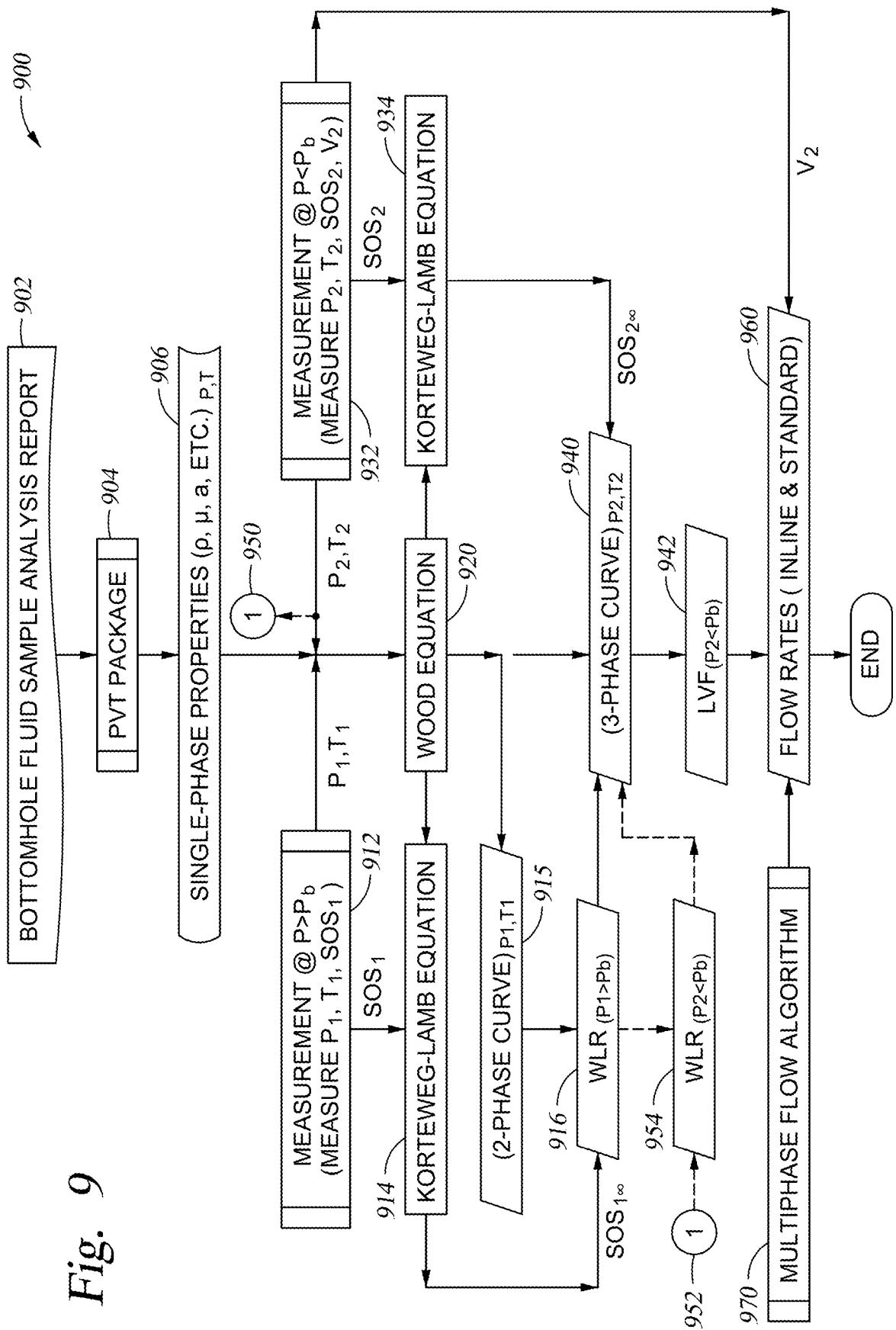
FIG. 9 illustrates example operations for determining phase flow rates for a given flow condition, in accordance with aspects of the present disclosure.

FIG. 9 illustrates example operations 900 for determining phase flow rates for a given flow condition, according to aspects of the present disclosure. At 902, a bottomhole fluid (e.g., a fluid mixture) sample analysis report may be obtained. Data from the bottomhole fluid sample analysis report may be analyzed with a PVT software package at 904 to determine single-phase properties (e.g., density, $\rho$; viscosity, $\mu$; speed of sound, a; and volume formation and retrograde condensation factors from reservoir to surface) of the analyzed mixture at various pressures (P) and temperatures (T), such as pressures and temperatures at the first location, the second location, the separator, and standard pressures and temperatures. The single-phase properties are represented at 906.

At 912, one or more sensors (e.g., the flowmeter 130 shown in FIG. 1) may measure the pressure ($P_1$), temperature ($T_1$), and SoS in the medium in the pipe ($SoS_1$) of the fluid mixture at a first location (e.g., location 114 shown in FIG. 1), where $P_1 > P_b$. Single-phase properties corresponding to $P_1$ and $T_1$ may be selected from a database of single-phase properties of components of the fluid mixture (this database may be, e.g., based on the bottomhole fluid sample analysis report at 902 or generated by the analyzer 194 shown in FIG. 1). 2-phase curves for the materials in the fluid mixture may be generated based on the selected single-phase properties at 915, and the solution envelope (e.g., the solution envelope 710) of the application may be created based on the selected single-phase properties. The selected single-phase properties along with the $SoS_1$ may then be used with the Wood equation, at 920, and the Korteweg-Lamb equation, at 914, to determine the WLR at the first station, at 916, and as discussed above with reference to Equation (20).

At 932, $P_2$, $T_2$, $SoS_2$, and a bulk fluid velocity, $V_2$, may be measured by one or more sensors (e.g., the flowmeter 160 shown in FIG. 1) at a second location (e.g., location 164 shown in FIG. 1), where $P_2 < P_b$. The measurements at 932 may be made, for example, shortly after or concurrently with the measurements at 912. Single-phase properties corresponding to $P_2$ and $T_2$ may be selected from the database of single-phase properties, 3-phase curves of the fluid mixture may be generated based on the selected single-phase properties (corresponding to $P_2$ and $T_2$) at 940, and a slightly different solution envelope of the application may be created. The selected single-phase properties (corresponding to $P_2$ and $T_2$) along with the $SoS_2$ and the WLR obtained earlier at 916 may be used with the Wood equation, at 920, and the Korteweg-Lamb equation, at 934, to determine the LVF (also referred to as the inline LVF) at the second station, at 942, and as discussed above with reference to Equation (23).

There may be a slight difference between the WLR values obtained at the first location and the second location, due to the difference in pressure. If the two locations are too far from each other and the $P_2$ at the second location is significantly lower than $P_b$, it is possible to determine WLR at the second location (i.e., WLR ($P_2<P_b$)) using a first-order linear interpolation along the pressure interval between the first location and the second location, at 954. (Details of how to perform such an interpolation may be found in US Pat. Pub. No. 2021/0381867 A1 or *SPE Production & Operations* Vol. 36, Issue 2, pp. 437-450, available at doi.org/10.2118/201313-PA). In this case, WLR at the second location may be determined based on WLR at the first location, pressure at the second location ($P_2$), and temperature at the second location ($T_2$). This optional process of converting WLR ($P_1>P_b$) to WLR ($P_2<P_b$) is shown by the dotted lines and the connection points 1 at 950 and 952 in FIG. 9.

Once the (LVF, WLR) pair of values as well as the mixture density are determined, the inline volumetric and mass phase flow rates may be calculated, at 960, using the measured $V_2$ and the cross-sectional area at the second location. It is also possible to implement various multiphase flow algorithms, at 970, to consider possible slip conditions between the phases, for calculating the flow rates at 960.

In a special case, the described techniques may be used with a single measurement device at a single location, if the pressure at the single location fluctuates around $P_b$ such that $P_{t2}<P_b<P_{t1}$ where t1 refers to a specific time when $P_{t1}>P_b$ and t2 refers to a different specific time when $P_{t2}<P_b$. In such circumstances, a single device, measuring SoS and fluid velocity at the single location, may be sufficient because the device measurements at different times may be used to resolve 3-phase flow rates. When $P=P_{t1}>P_b$ the flow is a 2-phase flow, and the location effectively functions as the first location at time t1 (i.e., an effective first location). The WLR is calculated from the 2-phase solution curve, and the device continues to report 2-phase in-situ flow rates. When $P=P_{t2}<P_b$ the flow is a 3-phase flow, and the location effectively functions as the second location at time t2 (i.e., an effective second location). This triggers the current methodology such that the previous WLR measurement from time t1 is used as an input to the measurements at time t2. With the known WLR from time t1, the other phase fraction LVF can be determined using the 3-phase solution domain as described earlier. The device then reports 3-phase in-situ flow rates.

Figure 10:
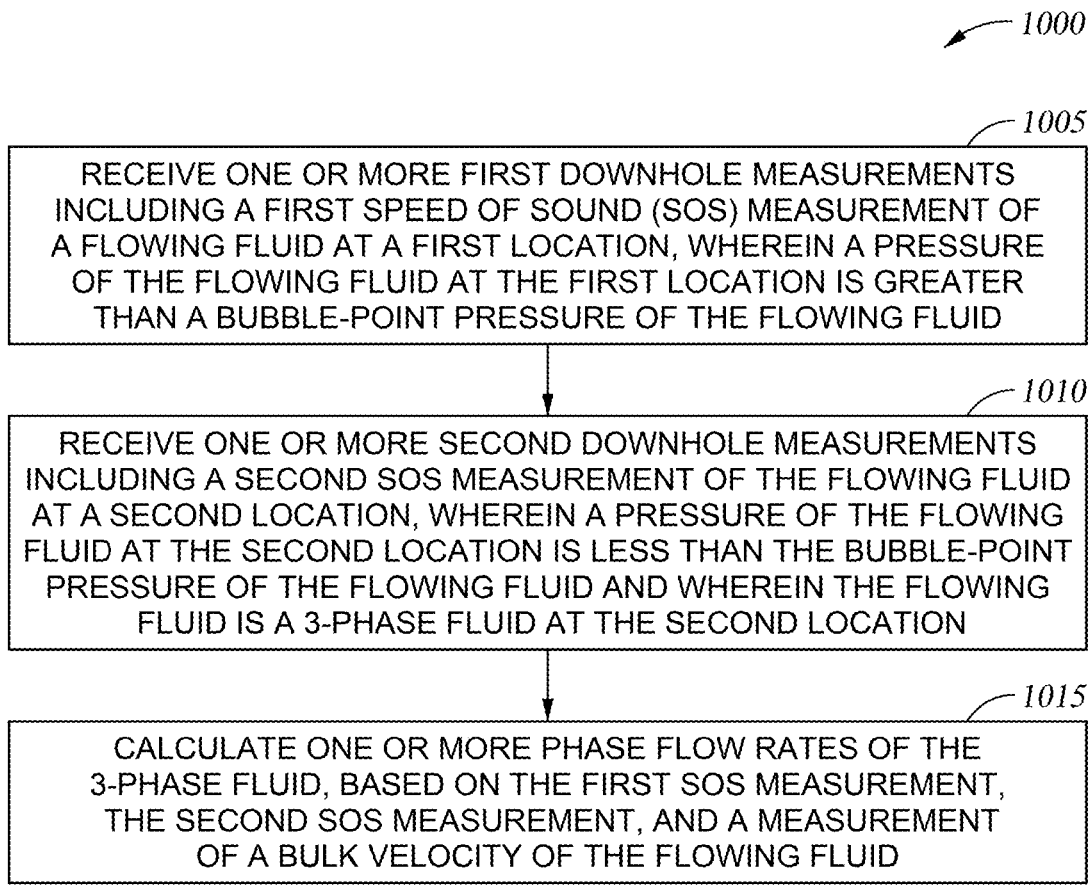
FIG. 10 illustrates example operations for hydrocarbon monitoring, in accordance with aspects of the present disclosure.

FIG. 10 illustrates example operations 1000 for hydrocarbon monitoring, in accordance with aspects of the present disclosure. Operations 1000 may be performed by a processing system (e.g., processor 112) and/or other components of a system for performing hydrocarbon monitoring. For example, one or more sensors (e.g., flowmeters 130 and 160 illustrated in FIG. 1) may provide the measurements.

Operations 1000 may begin at block 1005 by receiving one or more first downhole measurements including a first speed of sound (SoS) measurement of a flowing fluid at a first location. A pressure of the flowing fluid at the first location is greater than a bubble-point pressure of the flowing fluid. For example, processor 112 (see FIG. 1) may receive measurements of SoS of the fluid 110 in the conduit 105 ($SoS_1$) at the first location 114 from the flowmeter 130.

At block 1010, operations 1000 continue by receiving one or more second downhole measurements including a second SoS measurement of the flowing fluid at a second location. A pressure of the flowing fluid at the second location is less than the bubble-point pressure of the flowing fluid, such that the flowing fluid may be a 3-phase fluid mixture at the second location. Continuing the example from above, the processor 112 may receive measurements of SoS of the fluid 110 in the conduit 105 ($SoS_2$) at the second location 164 from the flowmeter 160.

Operations 1000 continue at block 1015 by calculating one or more phase flow rates of the 3-phase fluid mixture, based on the first SoS measurement, the second SoS measurement, and a measurement of a bulk velocity of the flowing fluid. Continuing the example, the processor may calculate a gas volumetric flow rate ($Q_g$), an oil volumetric flow rate ($Q_o$), and a water volumetric flow rate ($Q_w$) based on the first SoS measurement received from flowmeter 130, the second SoS measurement received from the flowmeter 160, and the bulk velocity ($V_2$) received from the flowmeter 160.

According to aspects of the present disclosure, a device or system performing operations 1000 may further determine a first inline phase fraction of the flowing fluid at the first location based on the first downhole measurements. For some aspects, the first inline phase fraction may be a water-in-liquid ratio (WLR) (e.g., WLR at 916). For some aspects, the first downhole measurements may further include a temperature (e.g., $T_1$) of the flowing fluid at the first location and a pressure (e.g., $P_1$) of the flowing fluid at the first location. In this case, determining the first inline phase fraction of the flowing fluid at the first location may be based on the first SoS measurement, the temperature of the flowing fluid at the first location, the pressure of the flowing fluid at the first location, and single-phase properties of components of the flowing fluid (e.g., single-phase properties 906). For some aspects, determining the first inline phase fraction may include: calculating a speed of sound (SoS) in an infinite medium based on the Wood and Korteweg-Lamb equations and the first downhole measurements; and determining the first inline phase fraction based on the SoS in the infinite medium, the first downhole measurements, and single-phase properties of components of the flowing fluid.

According to certain aspects, the second downhole measurements of block 1010 may further include a temperature (e.g., $T_2$) of the flowing fluid at the second location, a pressure (e.g., $P_2$) of the flowing fluid at the second location, and the measurement of the bulk velocity (e.g., $V_2$) of the flowing fluid at the second location. For some aspects, the operations 1000 further include determining a first inline phase fraction (e.g., WLR at 916) of the flowing fluid at the first location based on the first downhole measurements of block 1005; and determining an inline liquid volume fraction (LVF) (e.g., LVF at 942) of the flowing fluid, based on the first inline phase fraction or a second inline phase fraction (e.g., WLR at 954), the second downhole measurements, and single-phase properties of components of the flowing fluid. For some aspects, determining the LVF of the flowing fluid is based on the first inline phase fraction. For other aspects, the operations 1000 further include determining the second inline phase fraction based on the first inline phase fraction, the temperatures of the flowing fluid at the first and second locations, and the pressures of the flowing fluid at the first and second locations. In this case, determining the LVF of the flowing fluid may be based on the second inline phase fraction (e.g., the first inline phase fraction adjusted to second location pressure and temperature conditions, for example, by performing linear interpolation based on pressures and temperatures). For some aspects, determining the inline LVF comprises: calculating a speed of sound (SoS) in an infinite medium based on the Wood and Korteweg-Lamb equations and the second downhole measurements of block 1010; and determining the inline LVF based on the SoS in the infinite medium, the second downhole measurements, and the single-phase properties of components of the flowing fluid. For some aspects, the operations 1000 further include determining the single-phase properties of components of the flowing fluid based on an analysis of a bottomhole fluid sample (e.g., the bottomhole fluid sample at 902).

According to certain aspects, the first location and the second location are a same physical location. In this case, receiving the first downhole measurements of block 1005 may include receiving the first downhole measurements at a first time when the pressure is greater than the bubble-point pressure (e.g., at a first effective location); and receiving the second downhole measurements of block 1010 may include receiving the second downhole measurements at a second time when the pressure is less than the bubble-point pressure (e.g., at a second effective location), the second time being different from the first time.

According to certain aspects, at least one of the first downhole measurements of block 1005 or the second downhole measurements of block 1010 are received from an optical flowmeter.

According to certain aspects, at least one of the first downhole measurements of block 1005 or the second downhole measurements of block 1010 are received from a distributed acoustic sensing (DAS) coil.

Example Techniques for Modifying a Hydrocarbon Monitoring System to Determine Downhole 3-Phase Flow Rates A previously existing hydrocarbon monitoring system using an optical flowmeter (OFM) may be modified to operate in accordance with aspects of the present disclosure. The OFM in such a system may have been installed at a location where the pressure is greater than the bubble-point pressure ($P>P_b$). At this pressure, there is no free gas in the medium, the fluid flow is 2-phase, and the fluid is a mixture of oil and water. However, if the pressure in the well decreases below the bubble-point pressure ($P<P_b$), as commonly occurs as a well ages, then the flow becomes a 3-phase flow, due to the fluid effervescing. As a result, the OFM, which accurately measured the previously occurring 2-phase flow, will not be able to resolve the 3-phase flow rates by itself. Modifying such a system may entail installing one or more other sensors (e.g., a new OFM or a DAS line) into the well at a new location (e.g., deeper than the location of the previously installed OFM), where the pressure of the flowing fluid is greater than $P_b$. The processing system of the hydrocarbon monitoring system may then be modified (e.g., configured) to calculate one or more phase flow rates of the 3-phase fluid mixture, based on a first speed of sound (SoS) measurement of the flowing fluid at the original location received from the previously installed OFM, a second SoS measurement of the flowing fluid at the new location received from the newly installed sensor(s), and a measurement of a bulk velocity of the flowing fluid (e.g., provided by the OFM or the newly installed sensor(s)), in accordance with aspects of the present disclosure.

Figure 11:
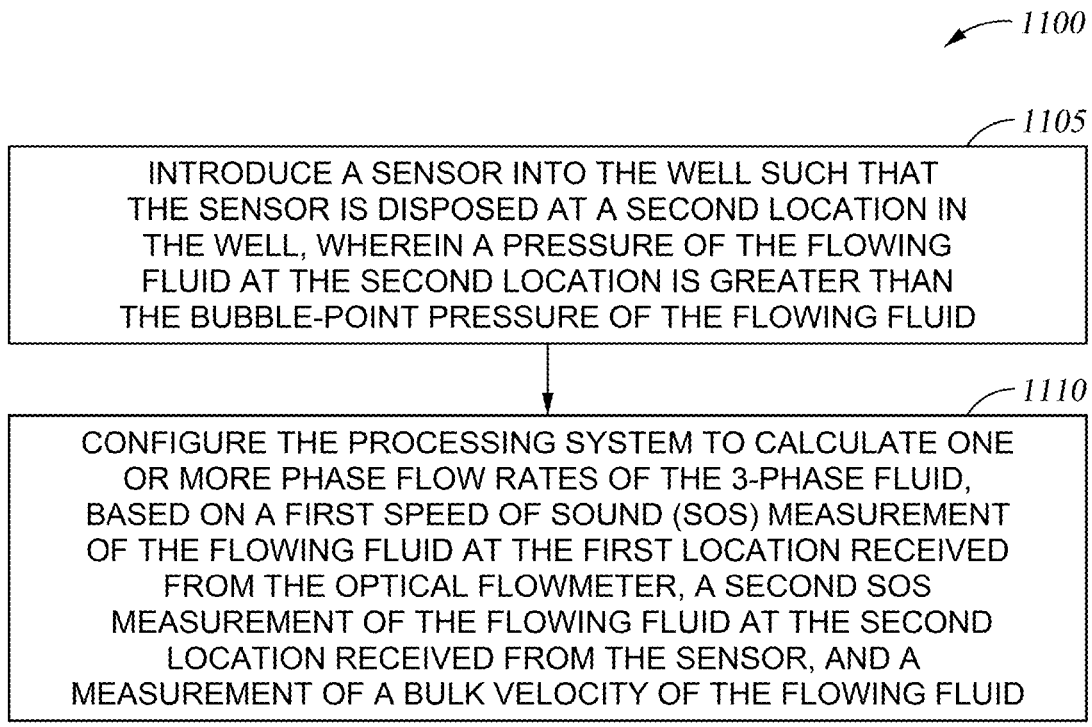
FIG. 11 illustrates example operations for modifying a hydrocarbon monitoring system, in accordance with aspects of the present disclosure.

FIG. 11 illustrates example operations 1100 for modifying a hydrocarbon monitoring system, in accordance with aspects of the present disclosure. The hydrocarbon monitoring system may already include an optical flowmeter disposed at a first location in a well and may also include a processing system. A pressure of a flowing fluid at the first location may be less than a bubble-point pressure of the flowing fluid ($P<P_b$), such that the flowing fluid may be a 3-phase fluid mixture at the first location. Operations 1100 may be performed, for example, by an operator of a well and/or various components of a hydrocarbon monitoring system. An operator may, for example, install or modify the flowmeters 130 and 160 illustrated in FIG. 1 and/or configure (or reconfigure) a processing system (e.g., a processing system including the processor 112 illustrated in FIG. 1).

Operations 1100 may begin at block 1105 by introducing a sensor into the well such that the sensor is disposed at a second location in the well, wherein a pressure of the flowing fluid at the second location is greater than the bubble-point pressure of the flowing fluid ($P>P_b$). For example, a well operator may install a flowmeter 130 (see FIG. 1) into a wellbore at a location 114, wherein a pressure of the flowing fluid 110 at the location 114 is greater than the bubble-point pressure of the flowing fluid.

At block 1110, operations 1100 continue by configuring the processing system to calculate one or more phase flow rates of the 3-phase fluid mixture, based on a first speed of sound (SoS) measurement of the flowing fluid at the first location received from the optical flowmeter, a second SoS measurement of the flowing fluid at the second location received from the sensor, and a measurement of a bulk velocity of the flowing fluid. Continuing the example from above, the well operator may update software to configure the processor 112 (see FIG. 1) to calculate a gas volumetric flow rate ($Q_g$), an oil volumetric flow rate ($Q_o$), and a water volumetric flow rate ($Q_w$) based on a first SoS measurement of the flowing fluid at the first location received from the optical flowmeter 160, a second SoS measurement of the flowing fluid at the second location received from the flowmeter 130, and a measurement of a bulk velocity of the flowing fluid.

According to certain aspects, the sensor of block 1105 may include an optical waveguide of a distributed acoustic sensing (DAS) system. For some aspects, introducing the sensor in block 1105 includes introducing the optical waveguide of the DAS system on a same optical waveguide communicatively coupled to the optical flowmeter. For some aspects, the optical waveguide comprises a DAS coil or DAS line and introducing the sensor in block 1105 includes disposing the DAS coil or DAS line at the second location.

According to certain aspects, introducing the sensor in block 1105 includes introducing a distributed acoustic sensing (DAS) waveguide into the well, separate from a waveguide communicatively coupled to the optical flowmeter.

According to certain aspects, configuring the processing system in block 1110 further includes configuring the processing system to calculate the one or more phase flow rates based on measurements of pressure and temperature of the flowing fluid at the second location.

The methodology disclosed herein has significant advantages over traditional methods, as described herein.

3-Phase Flow Measurement: The disclosed techniques enable 3-phase flow measurement by utilizing multiple SoS measurements along the well by using same sensor technology at multiple locations or combining different sensor technologies. A special case may occur in the field when the pressure at the device location fluctuates around $P_b$ (i.e., $P_{t2} < P_b < P_{t1}$). In this case, a single device, measuring SoS and velocity at a single location, may be used at different times to resolve the 3-phase flow.

Independent of Sensor Type: The disclosed techniques are independent of the sensor type as long as the sensors measure SoS, such as DAS systems and OFMs.

Existing Wells and Fiber Infrastructure: The methodology disclosed herein can be applied to existing wells and optical infrastructure by adding an appropriate topside optoelectronics system.

Nonnuclear 3-Phase Solution: The 3-phase flow measurement does not require any nuclear-based measurement such as gamma densitometers, so there are no regulatory concerns.

High Turndown Ratio: In its typical use with DAS systems and/or OFM systems, the turndown ratio (ratio of maximum flow rate to minimum flow rate) is high compared to Venturi-based systems.

Minimum Pressure Loss: In its typical use with DAS systems and/or OFM systems, the pipe geometry is fullbore, and there is no pressure loss when compared to Venturi-based systems.

Better Economics: The methodology disclosed herein uses minimum additional equipment when a DAS system is involved, if bulk velocity measurement is available.

CONCLUSION

Certain aspects of the present disclosure provide a flow algorithm for calculating phase flow rates for a 3-phase flow based on SoS measurements of the fluid mixture at a pressure greater than the bubble-point pressure ($P_b$) and SoS measurements at a pressure less than $P_b$.

Any of the operations described above, such as the operations 1000 of FIG. 10, may be included as instructions in a computer-readable medium for execution by a processor (e.g., processor 112 of FIG. 1) or any other suitable processing system. The computer-readable medium may comprise any suitable memory for storing instructions, such as read-only memory (ROM), random access memory (RAM), flash memory, an electrically erasable programmable ROM (EEPROM), a compact disc ROM (CD-ROM), or a floppy disk.

While the foregoing is directed to aspects of the present disclosure, other and further aspects may be devised without departing from the basic scope thereof, and the scope thereof is determined by the claims that follow.

The invention claimed is:

1. A method of hydrocarbon monitoring, comprising:
receiving one or more first downhole measurements including a first speed of sound (SoS) measurement of a flowing fluid at a first location, wherein a pressure of the flowing fluid at the first location is greater than a bubble-point pressure of the flowing fluid;
receiving one or more second downhole measurements including a second SoS measurement of the flowing fluid at a second location, wherein a pressure of the flowing fluid at the second location is less than the bubble-point pressure of the flowing fluid and wherein the flowing fluid is a 3-phase fluid mixture at the second location, wherein at least one of the one or more first downhole measurements or the one or more second downhole measurements is received from a downhole sensor; and
calculating one or more phase flow rates of the 3-phase fluid mixture, based on the first SoS measurement, the second SoS measurement, and a measurement of a bulk velocity of the flowing fluid.

2. The method of claim 1, further comprising determining a first inline phase fraction of the flowing fluid at the first location based on the one or more first downhole measurements.

3. The method of claim 2, wherein the first inline phase fraction is a water-in-liquid ratio (WLR).

4. The method of claim 2, wherein:
the one or more first downhole measurements further comprise a temperature of the flowing fluid at the first location and a pressure of the flowing fluid at the first location; and
determining the first inline phase fraction of the flowing fluid at the first location is based on the first SoS measurement, the temperature of the flowing fluid at the first location, the pressure of the flowing fluid at the first location, and single-phase properties of components of the flowing fluid.

5. The method of claim 2, wherein determining the first inline phase fraction comprises:
calculating a speed of sound (SoS) in an infinite medium based on the Wood and Korteweg-Lamb equations and the first downhole measurements; and
determining the first inline phase fraction based on the SoS in the infinite medium, the one or more first downhole measurements, and single-phase properties of components of the flowing fluid.

6. The method of claim 1, wherein the one or more second downhole measurements further comprise a temperature of the flowing fluid at the second location, a pressure of the flowing fluid at the second location, and the measurement of the bulk velocity of the flowing fluid at the second location.

7. The method of claim 6, further comprising:
determining a first inline phase fraction of the flowing fluid at the first location based on the one or more first downhole measurements; and
determining an inline liquid volume fraction (LVF) of the flowing fluid, based on (a) the first inline phase fraction or a second inline phase fraction, (b) the one or more second downhole measurements, and (c) single-phase properties of components of the flowing fluid.

8. The method of claim 7, wherein determining the LVF of the flowing fluid is based on the first inline phase fraction.

9. The method of claim 7, further comprising determining the second inline phase fraction based on the first inline phase fraction, the temperatures of the flowing fluid at the first and second locations, and the pressures of the flowing fluid at the first and second locations, wherein determining the LVF of the flowing fluid is based on the second inline phase fraction.

10. The method of claim 7, wherein determining the inline LVF comprises:
calculating a speed of sound (SoS) in an infinite medium based on the Wood and Korteweg-Lamb equations and the second downhole measurements; and
determining the inline LVF based on the SoS in the infinite medium, the one or more second downhole measurements, and the single-phase properties of components of the flowing fluid.

11. The method of claim 7, further comprising determining the single-phase properties of components of the flowing fluid based on an analysis of a bottomhole fluid sample.

12. The method of claim 1, wherein:
the first location and the second location are a same location;
receiving the one or more first downhole measurements comprises receiving the one or more first downhole measurements at a first time when the pressure is greater than the bubble-point pressure; and
receiving the one or more second downhole measurements comprises receiving the one or more second downhole measurements at a second time when the pressure is less than the bubble-point pressure, the second time being different from the first time.

13. The method of claim 1, wherein at least one of the one or more first downhole measurements or the one or more second downhole measurements is received from an optical flowmeter as the downhole sensor.

14. The method of claim 1, wherein at least one of the one or more first downhole measurements or the one or more second downhole measurements is received from a distributed acoustic sensing (DAS) coil as the downhole sensor.

15. A processing system for hydrocarbon monitoring, the processing system being configured to:
receive one or more first downhole measurements including a first speed of sound (SoS) measurement of a flowing fluid at a first location, wherein a pressure of the flowing fluid at the first location is greater than a bubble-point pressure of the flowing fluid;
receive one or more second downhole measurements including a second SoS measurement of the flowing fluid at a second location, wherein a pressure of the flowing fluid at the second location is less than the bubble-point pressure of the flowing fluid and wherein the flowing fluid is a 3-phase fluid mixture at the second location, wherein at least one of the one or more first downhole measurements or the one or more second downhole measurements is received from a downhole sensor; and
calculate one or more phase flow rates of the 3-phase fluid mixture, based on the first SoS measurement, the second SoS measurement, and a measurement of a bulk velocity of the flowing fluid.

16. A non-transitory computer-readable medium comprising instructions executable by a processing system to perform operations for hydrocarbon monitoring, the operations comprising:
receiving one or more first downhole measurements including a first speed of sound (SoS) measurement of a flowing fluid at a first location, wherein a pressure of the flowing fluid at the first location is greater than a bubble-point pressure of the flowing fluid;
receiving one or more second downhole measurements including a second SoS measurement of the flowing fluid at a second location, wherein a pressure of the flowing fluid at the second location is less than the bubble-point pressure of the flowing fluid and wherein the flowing fluid is a 3-phase fluid mixture at the second location, wherein at least one of the one or more first downhole measurements or the one or more second downhole measurements is received from a downhole sensor; and
calculating one or more phase flow rates of the 3-phase fluid mixture, based on the first SoS measurement, the second SoS measurement, and a measurement of a bulk velocity of the flowing fluid.

17. A method of modifying a hydrocarbon monitoring system comprising an optical flowmeter disposed at a first location in a well and a processing system, wherein a pressure of a flowing fluid at the first location is less than a bubble-point pressure of the flowing fluid and wherein the flowing fluid is a 3-phase fluid mixture at the first location, the method comprising:
introducing a sensor into the well such that the sensor is disposed at a second location in the well, wherein a pressure of the flowing fluid at the second location is greater than the bubble-point pressure of the flowing fluid; and
configuring the processing system to calculate one or more phase flow rates of the 3-phase fluid mixture, based on a first speed of sound (SoS) measurement of the flowing fluid at the first location received from the optical flowmeter, a second SoS measurement of the flowing fluid at the second location received from the sensor, and a measurement of a bulk velocity of the flowing fluid.

18. The method of claim 17, wherein the sensor comprises an optical waveguide of a distributed acoustic sensing (DAS) system.

19. The method of claim 18, wherein introducing the sensor comprises introducing the optical waveguide of the DAS system on a same optical waveguide communicatively coupled to the optical flowmeter.

20. The method of claim 18, wherein the optical waveguide comprises a DAS coil or a DAS line; and wherein introducing the sensor comprises disposing the DAS coil or the DAS line at the second location.

21. The method of claim 17, wherein introducing the sensor comprises introducing a distributed acoustic sensing (DAS) waveguide into the well, separate from a waveguide communicatively coupled to the optical flowmeter.

22. The method of claim 17, wherein configuring the processing system further comprises configuring the processing system to calculate the one or more phase flow rates based on measurements of pressure and temperature of the flowing fluid at the second location.

* * * * *